US007295311B2

(12) United States Patent
Nicoli et al.

(10) Patent No.: US 7,295,311 B2
(45) Date of Patent: Nov. 13, 2007

(54) METHODS AND APPARATUS FOR ELECTROPHORETIC MOBILITY DETERMINATION USING PHASE LIGHT SCATTERING ANALYSIS

(75) Inventors: David Nicoli, Goleta, CA (US); Yu-Jain Chang, Goleta, CA (US); Jau-Sien Wu, Santa Barbara, CA (US)

(73) Assignee: Particle Sizing Systems, Inc., Goleta, CA (US)

( * ) Notice: Subject to any disclaimer, the term of this patent is extended or adjusted under 35 U.S.C. 154(b) by 391 days.

(21) Appl. No.: 11/000,399

(22) Filed: Dec. 1, 2004

(65) Prior Publication Data

US 2006/0114467 A1 Jun. 1, 2006

(51) Int. Cl.
*G01N 21/00* (2006.01)
(52) U.S. Cl. .................................... 356/344
(58) Field of Classification Search .............. 356/28.5, 356/344, 445–448, 450
See application file for complete search history.

(56) References Cited

U.S. PATENT DOCUMENTS 3,732,014 A * 5/1973 Uzgiris .................. 356/336
4,097,153 A * 6/1978 DeRemigis ................ 204/549
5,215,883 A * 6/1993 Chu ........................... 204/452

* cited by examiner

*Primary Examiner*—Tarifur Chowdhury
*Assistant Examiner*—Jonathon D Cook
(74) *Attorney, Agent, or Firm*—Buchanan Ingersoll & Rooney PC

(57) ABSTRACT

An apparatus and method are disclosed for determining electrophoretic mobility using scattering light phase analysis comprising emitting a laser light along a path and transmitting a first portion of the laser light and reflecting a second portion of the laser light. The apparatus and method can also comprise deflecting one of the first and second portions of the laser in response to a drive signal, holding a sample to receive at least one of the first and second portions of the laser light under an electric field and output a composite light wave, outputting a photopulse signal based on the composite light wave, and measuring the electrophoretic mobility of the sample based on a phase shift analysis using cross-correlation of the photopulse signal with the drive signal.

51 Claims, 11 Drawing Sheets

METHODS AND APPARATUS FOR ELECTROPHORETIC MOBILITY DETERMINATION USING PHASE LIGHT SCATTERING ANALYSIS

BACKGROUND

FIELD

Phase light scattering analysis is disclosed for electrophoretic mobility determination, which involves passing a directed laser beam, or pair of laser beams, to a particulate matter in colloidal suspension under an electric field.

BACKGROUND INFORMATION

A wide variety of products include small particles, e.g., ranging mostly from 0.1 to 10 micrometers (microns, or μm) in size, that are suspended in a liquid. In many cases the liquid medium used to suspend the particles is predominantly water, usually containing added chemical components, including freely diffusing positive and negative ions. In cases where the particles are small enough to remain in suspension indefinitely, without naturally sedimenting, such systems are usually referred to as "colloidal" suspensions, or simply as "colloids".

In the case of aqueous suspensions, the physical mechanism most often responsible for keeping the particles effectively in indefinite suspension—i.e., stable with respect to significant agglomeration due to Van der Waals attractive forces—is electrostatic (Coulombic) repulsion. The particles are caused to carry either a net positive or negative electrical charge, by means of individual charged chemical groups attached thereto. These charged moieties may be chemically bonded to the particles (the "dispersed phase") or, alternatively, adsorbed onto their surfaces. The bonded or adsorbed moieties are often referred to as "titratable" groups, because the extent to which they are electrically charged depends on the pH of the surrounding aqueous medium (the "continuous phase"). For example, adsorbed molecules of an ionic surfactant, such as sodium dodecyl sulfate, may be used to impart a net charge to the particles—in this case a negative charge, due to the $SO_3^-$ moiety, after dissociation of $Na^+$ ions.

The stability of an aqueous suspension of charged particles can be dependent on the amount of charge carried by the particles. Insufficient charge, or electrical surface potential, may allow neighboring particles to diffuse close enough to each other to permit strong, close-range attractive forces to overcome the longer-range, but weaker, electrostatic repulsive forces acting between the particles, resulting in (usually irreversible) agglomeration. The extent to which Coulombic repulsive forces are dominant over Van der Waals attractive forces, described quantitatively by DLVO theory, depends strongly on the electrical potential, $\phi_0$, at the surfaces of the suspended particles. The Debye-Hückel "screening length", $\kappa^{-1}$, describes how steeply the electrical potential, $\phi(x)$, falls with increasing distance, x, from the particle surface (falling to $1/e$ of $\phi_o$ at $x=\kappa^{-1}$). The value of $\kappa^{-1}$, which defines the thickness of the electrical "double layer", is determined by the concentration of mobile counter-ions, which act to "screen" the electrical field produced by the particle, thus reducing its repulsive influence on a neighboring charged particle. Electrophoretic mobility measurements do not reveal directly the value of the surface potential, $\phi_o$. Rather, they determine the zeta potential, $\zeta$, defined as the value of the electrical potential, $\phi(x)$, at the "shear plane", an imaginary surface surrounding the particle which, in effect, "contains" some oppositely-charged counter-ions that are attracted to the particle. Therefore, $\zeta$ is reduced (in absolute value) relative to $\phi_0$. The greater the concentration of free (added) ions, the shorter the screening length, $\kappa^{-1}$, and the smaller the value of $\zeta$ relative to $\phi_o$. Notwithstanding this limitation, however, $\zeta$ usually acts as an effective proxy for the underlying quantity of interest, $\phi_o$.

The quality of a product or process based on a suspension of particles can depend on the extent to which the suspension resists agglomeration over time. Therefore, the ability to determine accurately the value of the zeta potential, $\zeta$, can be used to predict the stability, and therefore ultimately the quality, of the suspension of particles. Techniques have been previously developed, whereby an electric field is applied to an aqueous suspension of charged particles and an incident light beam, or pair of intersecting light beams, is also applied to the same region of the suspension. The particles give rise to scattered light waves, and the scattered wave that propagates at a particular angle is detected and analyzed by one or another means in order to determine the velocity of the particles resulting from application of the electric field. These "electrophoretic light scattering" (ELS) techniques are based on electrophoresis—i.e., the measurement of particle translation due to an applied electric field.

An ELS-based technique can be used to determine the electrophoretic mobility, μ, which relates the steady-state velocity of a charged particle caused by application of an electric field to the strength of that field. The force exerted by the electric field on the particle is proportional to the strength of the field, E, while the viscous (Stokes) drag force resisting the field-induced motion is proportional to the velocity of the particle. Equilibrium is achieved when the particle velocity increases to a value where the two opposing forces become equal, resulting in zero net force and no further acceleration of the particle. Hence, the equilibrium velocity, v, is proportional to the magnitude of the applied electric field, E, where the constant of proportionality, μ, is referred to as the electrophoretic mobility, $$v=\mu E. \quad (1)$$

The value of μ is determined for a particle suspension of interest. The values of the velocity and electric field strength are usually expressed in units of cm/sec and volt/cm, respectively, resulting in electrophoretic mobilities that are expressed in units of cm/sec/volt/cm. However, the particle velocity is very small (i.e., <<1 cm/sec), usually falling in the range of 1 to 100 microns/sec: Therefore, it is convenient to express the value of μ in terms of a "mobility unit", or M.U., equal to 1 micron/sec/volt/cm, or $10^{-4}$ cm/sec/volt/cm.

The zeta potential, $\zeta$, can be computed from μ. In general, the relationship between μ and $\zeta$ is complicated (given by Henry's Equation), as it depends on the extent of overlap of the electrical double layers of neighboring particles, and therefore on the concentration of mobile ions in the suspension. For applications of practical interest, the ionic strength of the particle suspension is often significant, resulting in a small value of $\kappa^{-1}$, and therefore $\kappa a>>1$ (with a=particle diameter), so that there is negligible overlap of the electrical double layers. The Smoluchowski approximation is then valid, and the desired quantity, $\zeta$, is simply proportional to μ, i.e., $\zeta=(\eta/\epsilon)\mu$, where $\eta$ is the viscosity, and $\epsilon$ the dielectric constant of the fluid—approximately 0.01 Poise and 80, respectively, for aqueous suspensions (20-deg C.). For example, in the case of 100-nm particles suspended in aqueous suspension with 0.001M added salt (e.g., KCl), $\kappa^{-1}=10$ nm and $\kappa a=10$, which satisfies the Smoluchowski condition.

The principles underlying electrophoretic mobility determination by laser light scattering are reviewed by Miller et al, J. Colloid and Interface Science, 143, #2, pp. 532-554 (1991). The method of laser-Doppler velocimetry (LDV) for determining quantity µ measures the shift in the frequency of light scattered by particles as they move through an interference "fringe" pattern of alternating bright and dark regions created by two crossed laser beams. As pointed out by Miller et al, the frequency shift method has a limitation, in that it becomes inaccurate and/or ineffective when the particle velocity is very small. This is the case either when the mobility is very small (e.g., organic fluid suspensions) or when the applied electric field must be kept very low to avoid excessive Joule heating (e.g., aqueous suspensions containing significant electrolyte concentration). Miller et al introduce a new method for determining electrophoretic mobilities, called phase analysis light scattering (PALS), that removes the restrictions inherent in the traditional frequency shift method and which can therefore measure much smaller particle velocities. The method taught by Miller et al is based on the use of a well-known signal processing technique known as "lock-in" (or phase sensitive) detection. Consequently, their apparatus uses analog-based electronic systems that are relatively complex, expensive and that are limited in accuracy, resolution and reproducibility.

SUMMARY OF THE INVENTION

Exemplary methods and apparatus are disclosed for electrophoretic mobility determination using light scattering phase analysis. A device comprises, for example, a laser emitting laser light along a path, a beam splitter positioned along the path to transmit a first portion of the laser light and to reflect a second portion of the laser light, an oscillating mirror positioned to deflect one of the first and second portions of the laser light in response to a drive signal, a cuvette holding a sample disposed to output a composite light wave based on input of at least one of the first and second portions of the laser light, the cuvette having at least two electrodes disposed along sides of the cuvette to create an electric field, a scattered light detector disposed to output a photopulse signal based on input of the composite light wave; and a processor for measuring the electrophoretic mobility of the sample based on a phase shift analysis using cross-correlation of the photopulse signal with the drive signal.

An apparatus comprises, for example, means for emitting a laser light along a path, means for transmitting a first portion of the laser light and reflecting a second portion of the laser light, means for deflecting one of the first and second portions of the laser in response to a drive signal, means for holding a sample, to receive at least one of the first and second portions of the laser light under an electric field, and to output a composite light wave, means for outputting a photopulse signal based on the composite light wave, and means for measuring the electrophoretic mobility of the sample based on a phase shift analysis using cross-correlation of the photopulse signal with the drive signal.

A method comprises, for example, emitting a laser light along a path, transmitting a first portion of the laser light and reflecting a second portion of the laser light, deflecting one of the first and second portions of the laser in response to a drive signal, holding a sample to receive at least one of the first and second portions of the laser light under an electric field and output a composite light wave, outputting a photopulse signal based on the composite light wave, and measuring the electrophoretic mobility of the sample based on a phase shift analysis using cross-correlation of the photopulse signal with the drive signal.

BRIEF DESCRIPTION OF THE DRAWING FIGURES

The figures illustrate exemplary concepts and embodiments of light scattering analysis as disclosed, wherein.

DETAILED DESCRIPTION

Various aspects will now be described in connection with exemplary embodiments, including certain aspects described in terms of steps that can be performed by elements of a computer system. For example, it will be recognized that in each of the embodiments, computations and analyses can be performed by specialized circuits or circuitry, by program instructions being executed by one or more processors, or by a combination of both. Thus, the various aspects can be embodied in many different forms, and all such forms are contemplated to be within the scope of what is described.

In an exemplary embodiment, a particle moving under the influence of an applied electric field and illuminated by an incident laser light wave gives rise to a scattered light wave that is shifted in phase with respect to the incident wave. The extent of the phase shift depends on the angle of scattering, θ, and the velocity of the particle, v, which in turn depends on its electrophoretic mobility, µ, and the electric field strength, E. Of course, detection of the scattered light wave alone by a suitable light detection means is not able to determine the phase, or the time rate of change in the phase, of the wave. A suitable "frame of reference" is therefore established in accordance with exemplary embodiments disclosed herein so that the phase of the scattered light wave can, in effect, be compared to the phase of another light wave, which remains constant. A method and apparatus are disclosed herein for making this phase-based comparison.

Figure 1A:
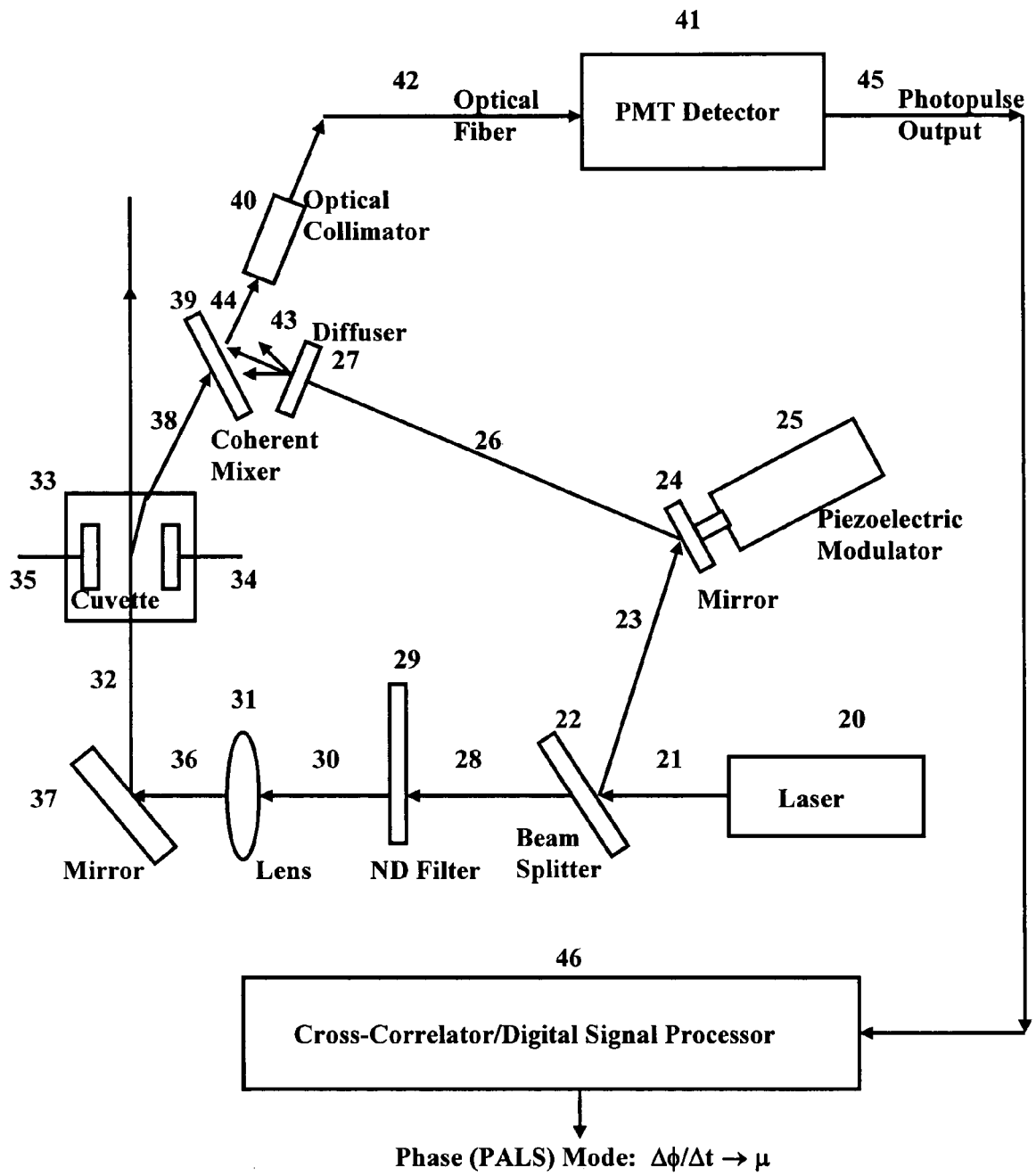
FIG. 1a shows a block diagram of an exemplary embodiment for light scattering analysis using cross-correlation for phase shift analysis of an optical detection signal.
Figure 1B:
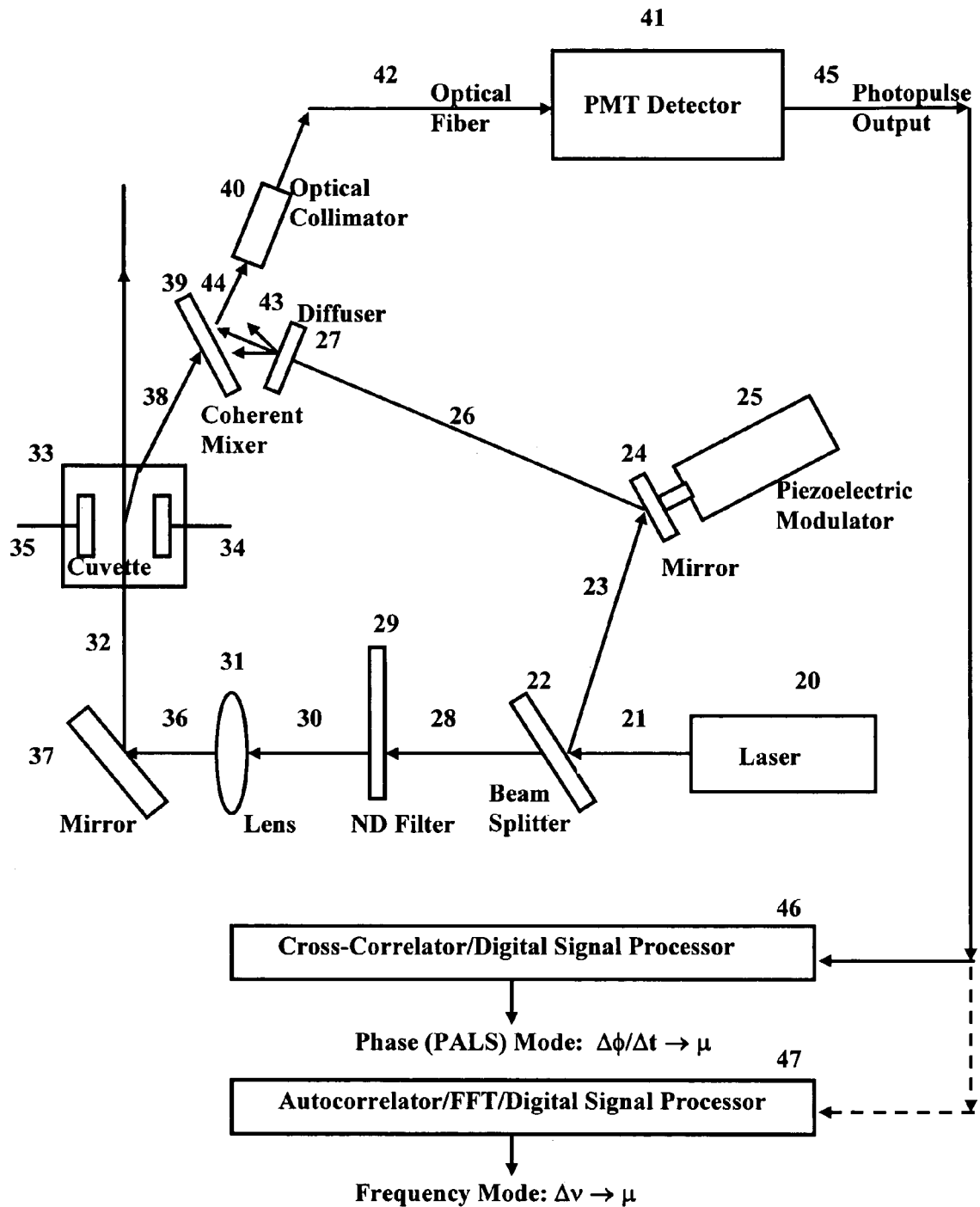
FIG. 1b shows a block diagram of another exemplary embodiment for light scattering analysis using autocorrelation for frequency shift analysis and cross-correlation for phase shift analysis of an optical detection signal.

FIGS. 1a and 1b show simplified block diagrams of an exemplary apparatus for light scattering analysis for analyzing electrophoretic light scattering based on electrophoretic mobility. The apparatus is represented as a device which includes a means, such as a laser 20, for emitting a laser light along a path. As shown, a collimated beam 21 of substantially coherent light of wavelength $\lambda_0$ (in vacuum), produced by the laser 20, is directed toward a means for beam diversion 22 positioned along the path to transmit a first portion of the laser light and to reflect a second portion of the laser light. The means for beam diversion (beam splitter) 22 can be chosen from a variety of optical elements, such as a beam splitter, a thin film laminated plate, a mirror, a prism, and any other optical element capable of diverting a portion of a beam. Moreover, the beam splitter 22 can be a window of suitable thickness, made of polished silica or other suitable transparent material. The beam splitter 22 gives rise to a reflected beam of light 23 of the same wavelength, having a relatively small fraction (e.g., 2 to 5%) of the intensity of the original light beam, directed toward a suitable means, such as a deflecting mirror 24. The latter is shown in FIGS. 1a and 1b as a front-surface mirror 24 attached to a suitable modulator 25 for modulating the oscillation of the mirror 24. The modulator can be a transducer means, such as a piezoelectric transducer 25. However, the transducer means can be chosen from a wide variety of transducers capable of responding to a driving signal. The position of the deflecting mirror 24 depends on the magnitude of the modulating voltage, $V_M$, applied to the piezoelectric transducer. The extent of linear extension (or contraction, depending on the sign of $V_M$) of the piezoelectric transducer means, and therefore the extent of translation of the deflecting mirror attached thereto, is approximately proportional to $V_M$, assuming an approximately linear response of the piezoelectric transducer 25.

Two substantially parallel, reflected beams of light 23 can be created by the beam splitter 22, owing to the fact that specular reflections occur at both the front and back surfaces of the beam splitter. One or more of these reflected light beams impinge upon the deflecting mirror 24, which is caused to oscillate back and forth in position by the modulator 25, to which it is attached. The resulting, preferably single reflected light beam 26, is referred to as the "reference" light wave. It is specularly reflected by the modulated deflecting mirror 24 and thereby directed, without substantial loss of intensity, to a light diffuser 27.

The portion of the original laser light beam that emerges from the beam splitter 22, having a typical intensity of approximately 95-98% of the original laser beam intensity, is directed to a filtering means, such as a variable neutral-density (ND) filter 29, which attenuates the laser light to output a filtered laser light. However, any optical filter capable of filtering optical light may be employed. The latter can be attached to a stepper motor or other suitable mechanically rotatable means, so that the variable ND filter can be rotated to a given angular position, in response to a control signal provided by a means for measuring the electrophoretic mobility of the sample, which can be any one of a variety of a digitally-based computing system, such as a processor or a digital signal processing microprocessor system. As further discussed, the means for measuring the electorphoretic mobility of the sample can be based on a phase shift analysis using cross-correlation of the photopulse signal with the drive signal. The substantially coherent laser light beam that emerges from the variable ND filter is thus able to be attenuated in intensity to a variable extent, depending on the degree of rotation of the variable ND filter 29. The resulting variably attenuated light beam 30 impinges on a means, such as a focusing lens 31, to focus the attenuated incident laser light beam 32 to a region within a means, such as a sample cuvette 33, where such region is approximately centered between two conducting electrodes 34 and 35 immersed in the particle suspension contained in the sample cuvette 33. A sample cuvette 33 holds a sample to receive at least one of the first and second portions of the laser light and have at least two electrodes disposed along sides of the sample cuvette to create an electric field. A switched electric potential applied between the two conducting electrodes 34 and 35 causes a switched electric field to be induced in the region of the cuvette 33 holding the particle suspension.

In FIGS. 1a and 1b, the laser light beam 36 emerging from the focusing lens 31 can be deflected, by a 90-degree angle for example, by a means, such as a fixed reflecting mirror 37, before it enters the sample cuvette 33. This front-surface mirror 37 may be employed to allow the apparatus to be more physically compact. However, another apparatus having the focused light beam 36 directed into the sample cuvette 33 can be employed without the change in direction. Both exemplary embodiments of FIGS. 1a and 1b can optionally be implemented without the reflecting mirror 37.

The focused laser light beam 32 entering the sample cuvette 33 impinges on some of the particles in liquid suspension, causing them to scatter a portion of the incident light beam. A small fraction of the scattered light 38 thus produced by the particles impinges on two pre-aligned optical components—a coherent mixer 39 and optical collector 40—located outside the sample cuvette 33. The optical collector can be any element capable of collecting a light wave, such as a grin lens, any one of collimators, a prism, an optical fiber, an optical lens, or any optical wave guide. These components together effectively comprise an optical receiver means. A (small) portion of the scattered light 38 which is radiated at a particular scattering angle, θ, can be collected by the optical receiver means and directed to a means, such as a scattered light detector 41, which receives a composite light wave from the cuvette and outputs a photopulse based on the received light. (For a sample cuvette having a square cross section, the "external" angle of the collected scattered light 38 is larger than the actual (internal) scattering angle, due to refraction of the scattered light beam leaving the liquid sample in the cuvette and entering the surrounding air, as shown in FIGS. 1a and 1b.) The resulting scattered light ray impinges on a means, such as a coherent mixer 39, passes through the latter and is collected by a means, such as an optical collector 40, from which it is directed, optionally by optical fiber means 42, to a means, such as a scattered light detector 41, which can be a photomultiplier tube (PMT) and associated electronics which outputs photopulses based on the received light. The coherent mixer 39 can be a beam splitter, similar to the optical element used to create the reference beam, described earlier. As such, it can have a transparent glass or silica window, which transmits the scattered light ray with minimal attenuation (typically with 95 to 98% of the intensity of the incident scattered light wave) before it impinges on a means, such as an optical collector 40, which is disposed at a scattering angle to collect a composite light wave. The latter can include a pinhole of suitable size, properly spaced and aligned with respect to the core of a means, such as an optical fiber 42 (e.g., multi-mode fiber), used to carry the light wave signal to the light detection means 41. Alternatively, the optical collector 40 can include a collimating lens attached to an optical fiber 42 (e.g., single-mode fiber), which is connected to the light detector 41.

The coherent mixer 39 serves to superpose, or coherently "mix", the arriving scattered light wave 38 with a light wave derived from the reference light beam 23, extracted from the laser 20 by a beam splitter 22 and deflected to a means, such as a light diffuser 27, by the modulated deflecting mirror 24. As suggested by its name, the purpose of the light diffuser 27 is to diffuse the reference light beam impinging on it, thus producing a "spray" of "secondary" reference light rays 43 that emerge in many directions from the light diffuser 27. The latter typically consists of a layer of translucent ("frosted") plastic or other partially opaque material of suitable thickness and composition. In the process of performing this light-diffusing function, the light diffuser 27 also can serve to attenuate to a substantial degree the intensity of the reference beam. Many of the resulting individual attenuated rays 43 that emerge from the light diffuser 27 over a range of directions impinge on the beam splitter means comprising the coherent mixer 39. Out of all of these rays, essentially a single attenuated reference light ray will be reflected from either the front or back surface of the beam splitter means so as to be substantially perfectly aligned with the scattered light wave (scattering angle θ) 38 that emerges from the sample cuvette. As a result, the oscillating electric field associated with this "selected", secondary reference light wave will be added by "coherent superposition" to the electric field associated with the scattered light wave. Each of the oscillating electric fields has a well-defined phase before they are coherently mixed. The resulting composite light wave 44, representing a coherent superposition of the two individual light waves, will be collected by the receiving optical collector 40 and directed to the light detector 41. In normal operation, the central controlling computer (e.g., microprocessor) adjusts the angular position of the variable ND filter 29 in order to adjust the level of average intensity of the light scattered at angle θ and subsequently collected and detected by the light detection means. This level can be adjusted to be approximately 5 to 10% of the intensity of the light contributed by the (diffused) reference light beam, where it is understood that the ratio of the intensities of the scattered light wave 38 and the "selected", secondary reference light wave 43 before coherent mixing is not critical. This ratio is typically pre-adjusted in order to optimize the signal-to-noise ratio of the resulting phase shift analysis.

The light diffuser 27 relaxes the constraint on the alignment of the reference light beam 23, 26 with respect to the collected scattered light wave in order to achieve coherent mixing of the two light waves. The diffuser 27, in effect, converts a single, relatively intense primary reference light beam 23, 26 into many individual, weaker, secondary reference light waves 43, each having a well-defined phase that is fixed with respect to the phase of the primary reference light beam 26 that impinges on the light diffuser 27. The resulting secondary reference light waves 43 emerge from the light diffuser 27 with a wide range of propagating directions, and only one of these secondary reference waves is required to mix successfully with the selected scattered light wave 38 prior to collection and detection. Therefore, one largely avoids the painstaking effort that otherwise may be needed to align the incident reference light beam with respect to the coherent mixer 39 in order to achieve successful coherent superposition with the scattered light wave 38 prior to collection by the optical collector 40. Indeed, the optical scheme of "mixing" a secondary reference light wave 43 with the scattered light wave 38 shown in FIGS. 1a and 1b resembles a classical interferometer. This device can involve considerable effort to achieve proper optical alignment of the light waves that one desires to bring into interference, or superposition. In any case, it can be sensitive to small shifts in the positions of the optical elements due to vibrations and thermal expansion. Use of the light diffuser 27 simplifies the task of achieving the needed optical alignment. In addition, the light diffuser means significantly reduces the intensity of the selected reference light wave (compared to the intensity of the starting reference light beam) that successfully mixes with the scattered light wave. This function is required because the intensity of the primary reference beam 23, 26 can be enormously greater than the intensity of the scattered light 38 produced by the suspended particles and collected by the optical collector means. The extent of the mismatch in intensities of the two waves must be reduced to allow for efficient processing of the detected light signal.

An exemplary embodiment described herein is based on processing the detected light signal, through use of a mathematical procedure known as the cross-correlation function (CCF). In the case of the first embodiment shown schematically in FIGS. 1a and 1b, an electronic representation 45 of the detected light signal is obtained from the coherent superposition of a scattered light wave 38 originating from particles moving under an applied electric field and a reference light wave 43 derived from the laser light source. The purpose of using the CCF is to measure the phase shift, $\Delta\phi$, that occurs in the scattered light wave 38 as a result of electric field-induced particle motion. From the resulting time rate of phase shift, $\Delta\phi/\Delta t$, a value of the electrophoretic mobility, $\mu$, can be obtained using phase analysis.

An ELS-based technique based on phase analysis exploits the effect of translation of a particle on the phase of the scattered light wave that it generates. Typically an incident light beam impinging on a single particle in liquid suspension gives rise to light scattered by that particle. The direction of propagation of the incident light wave, defining zero scattering angle (θ=0), is assumed to be along the y-axis, perpendicular to the x-axis. It is convenient to describe the incident light beam using the "wavevector" $\bar{k}_0$, which points in the direction of propagation of the incident light beam and has a magnitude, or length, equal to $2\pi/\lambda$, where $\lambda$ is the wavelength of the light beam in the liquid medium. An electric field, denoted by vector $\bar{E}$, having a magnitude, or length, E, is applied along the x-axis to the region of the suspension containing the particle. The particle is thus caused to move in the same direction as $\bar{E}$ (or opposite direction, depending on whether the particle is positively or negatively charged)—i.e., along the x-axis.

Scattered light rays, or waves, are generated by the particle at every position as it translates. The "original" scattered light ray originates from the particle at its "original" position, x=0, before it has been caused to move by an applied electric field. The "new" scattered light ray originates from the same particle after an elapsed time $\Delta t$, when it has reached a "new" position, x=$\Delta x$. In reality, the particle, regardless of its position, scatters light in all directions when exposed to the incident laser light beam. However, it is implicitly assumed that the detector responsible for detecting the scattered light rays, a) is located very far away relative to the very small particle translation, $\Delta x$, and b) has a very small detection aperture, thus resembling an ideal "point" detector. Therefore, the detector is able to receive and detect light only from those rays that effectively have the same scattering angle, $\theta$, and which are therefore very nearly parallel. The scattered light waves generated by the particle (regardless of its position, x) at all other scattering angles are unable to contribute to the detected signal. Implicit is the understanding that for any other intermediate position along the x-axis, $0<x<\Delta x$, the particle also scatters light, which therefore include scattered light rays having the same scattering angle, $\theta$, which are also detected by the means for outputting a photopulse signal based on the composite light wave (detector means).

The scattered light wave originating from the "new" particle position, $x=\Delta x$, has slightly less distance to travel in order to reach the detector means, compared to the scattered light wave originating from the "original" particle position, $x=0$. (For simplicity it is assumed that the scattering angle, $\theta$, is "positive", lying in the first quadrant of the x-y plane.) The phase of the incident light wave is the same as it impinges on the particle in its "original" position as when it impinges on the particle in its "new" position, because the x-axis of translation of the particle is parallel to the "wavefront" of the incident wave. Therefore, the two scattered waves possess the same (starting) phase when they are radiated by the particle at each of the two positions, $x=0$ and $x=\Delta x$. Hence, there is a difference in phase between the two scattered light rays when they arrive at the distant detector, easily related to the difference in the optical path length (OPL) between the particle and the detector. This path length difference, denoted by $\Delta L$, is related simply to the particle translation, $\Delta x$, and the scattering angle, $\theta$, $$\Delta L = \Delta x \sin \theta. \quad (2)$$

The propagation of a scattered light ray along a given direction (distance measured by L) is conveniently described using the familiar expression for propagating waves, $\exp[i(\omega t + kL)]$, where $\omega$ is the angular frequency ($\omega = 2\pi\nu$, where $\nu$ is the frequency) of the scattered wave and k the length of the scattered light wavevector, $2\pi/\lambda$. The real and imaginary parts of this expression yield the familiar sinusoidal waves in space (L) and time (t), $\sin(\omega t + kL)$ or $\cos(\omega t + kL)$, respectively. These sinusoidal expressions describe the change in the magnitude of the electric field associated with the light wave with respect to time (t) for a given location (L=fixed), or with respect to location (L) for a given time (t=fixed). Therefore, the shift in phase, $\Delta\phi$, of the "new" scattered light wave relative to the phase of the "original" scattered wave upon arrival at the detector, associated with translation of the particle by distance $\Delta x$, is given by $$\Delta\phi = k \Delta L. \quad (3)$$

From Equation 2, this becomes $$\Delta\phi = (2\pi/\lambda) \Delta x \sin \theta, \quad (4a)$$

or, equivalently, $$\Delta\phi = (2\pi n/\lambda_o) \Delta x \sin \theta, \quad (4b)$$

where n is the refractive index of the suspending liquid and $\lambda_o$ the wavelength of the laser light beam in vacuum (effectively, air).

This change in phase, $\Delta\phi$, is easily related to the electrophoretic mobility, $\mu$, using the definitions of the particle velocity, $v=\Delta x/\Delta t$, and of $\mu$ (Equation 1), resulting in $$\Delta x = v \Delta t = \mu E \Delta t. \quad (5)$$

From Equation 4b one obtains a simple relationship between the phase shift, $\Delta\phi$, between the two scattered light waves, the distance moved by the particle, $\Delta x$, and the time, $\Delta t$, needed for this movement for fixed values of parameters n, $\lambda_o$, and $\theta$ and for a given value of E, $$\Delta\phi = (2\pi n/\lambda_o)\mu E \Delta t \sin \theta. \quad (6)$$

Of course, during the application of an electric field, the particle doesn't move abruptly from its "original" to "new" position. Rather, it moves (ideally) at constant velocity, v, over the elapsed time, $\Delta t$, until the electric field reverses direction. Therefore, the relevant quantity to be measured is not the phase shift, $\Delta\phi$, per se, but rather the rateofchange of the phase shift, $\Delta\phi/\Delta t$, obtained easily from Equation 6, $$\Delta\phi/\Delta t = (2\pi n/\lambda_o)\mu E \sin \theta. \quad (7)$$

The quantity of interest, the electrophoretic mobility, $\mu$, obtained by inverting Equation 7, is therefore proportional to the rate of change of the phase shift, $\Delta\phi/\Delta t$, $$\mu = (1/E) (\lambda_o/2\pi n)(1/\sin \theta)\Delta\phi/\Delta t. \quad (8)$$

In the discussion above it was assumed that the change in x-axis position of the charged particle is caused solely by the force exerted by the applied electric field. However, it is well known that all particles in suspension engage in random, Brownian motion, due to collisions by surrounding solvent molecules. The smaller the particles, the greater the magnitude of this random, diffusive motion, which is completely unrelated to the motion induced by an applied electric field. Therefore, the scattering angle, $\theta$, is chosen to be very small (typically 10-15 degrees) for the ELS measurement, in order to minimize the unavoidable randomly occurring phase shifts in the scattered light waves arriving at the detector, caused by random changes in the particle positions due to Brownian motion. The effect of the scattering angle on the extent of the random phase shifts due to this uncorrelated, diffusive motion is discussed below.

Equation 8 relates simply the rate of change of the phase shift, $\Delta\phi/\Delta t$, of the detected scattered light wave and the magnitude, E, of the electric field giving rise to uniform particle motion to the desired electrophoretic mobility, $\mu$. It is instructive to calculate values of $\Delta\phi/\Delta t$ for typical values of $\mu$ and E, assuming $\lambda=635$ nm ($0.635\times10^{-4}$ cm), n=1.33 (water) and $\theta=14.06$-deg (angle utilized to obtain results to be shown later). For $\mu=1$ M.U. and E=10 V/cm, $\Delta\phi/\Delta t=32.1$ rad/sec, or 1.84 deg/msec For $\mu=1$ M.U. and E=1 V/cm, $\Delta\phi/\Delta t=3.21$ rad/sec, or 0.184 deg/msec In the foregoing phase analysis, it is useful to consider the simplifying case of stationary particles—i.e., assuming no applied electric field, and also the hypothetical absence of diffusion and convective drift. In order to determine the phase of the scattered light wave 38 relative to the phase of the reference light wave using the optical scheme shown in FIGS. 1a and 1b, the phase of the reference light wave 26 is perturbed in a chosen, periodic fashion. This perturbation is conveniently achieved using a periodic, linear-ramp voltage signal to drive the piezoelectric transducer 25, resulting in repetitive, uniform translation of the deflecting mirror 24 used to direct the reference light beam 26 onto the means for receiving a portion of the laser light and producing a diffused component of the portion of the laser light (light diffuser means). A driving signal (voltage), $V_M(t)$ vs. time, t, that is applied to the piezoelectric transducer 25, causes the front-surface mirror 24 to move back and forth. The simplest choice (out of many) for $V_M(t)$, is a periodic "sawtooth" waveform, in which the driving voltage increases approximately linearly with time, t, during an elapsed time $T_M$, the "period" of the periodic waveform. At the end of this time the driving voltage signal reaches a suitable preset maximum value, $V_{M,MAX}$ (the "amplitude"), and then it immediately falls to the starting value (zero or some minimum voltage). This behavior of $V_M(t)$ then repeats itself over successive time periods. Ideally, the assumed linear behavior of $V_M(t)$ vs. t, during each period results in a proportional linear translation of the deflecting mirror 24 attached to the modulating means. The assumed linear response of the piezoelectric transducer 25, or other modulating means, and consequent used linear translation of the deflecting mirror 24 attached thereto, is not required for successful determination of $\Delta\phi$ and $\Delta\phi/\Delta t$ using the exemplary CCF technique as disclosed herein.

The optical path length (OPL) of the reference light beam 23 and 26, from point "A" on the front (or back) surface of the means for transmitting a portion of the laser light and reflecting another portion of the laser light (beam splitter means) 22, to point "B" on the means for deflecting one portion of the laser light in response to a drive signal (deflecting mirror means) 24, to point "C" on the light diffuser means 27, therefore also changes linearly with time, t, due to drive signal $V_M(t)$. If the linear ramp (increase) in $V_M(t)$ vs. t causes progressive extension of the piezoelectric transducer 25 during the time period $T_M$, then the OPL of the reference beam will decrease linearly with time during that period. Conversely, if the linear ramp in $V_M(t)$ vs. t causes progressive contraction of the piezoelectric transducer 25 during the time period $T_M$, then the OPL of the reference beam will increase linearly with time during that period. In either case, the resulting (assumed) linear translation of the deflecting mirror position with increasing time during the period $T_M$ causes the phase, $\phi_{ref}$, of the secondary reference light wave (that mixes with the scattered light wave) generated by the light diffuser means to either increase or decrease linearly with time during the period $T_M$, depending on whether the OPL increases or decreases. It is implicitly assumed hereinafter that the maximum amplitude, $V_{M,MAX}$, of the modulator voltage drive signal is sufficiently large that the change in the OPL of the reference light wave will exceed (to some degree) the wavelength, $\lambda_o$, of the light. As a consequence, the phase of the reference light wave 26 will increase or decrease by at least $2\pi$ radians (360°)—representing at least one complete cycle of oscillation of the electric field associated with the reference light wave—over the period $T_M$.

When the reference light beam 26, having a phase, $\phi_{ref}$, that increases (or decreases) linearly and periodically with time, mixes coherently with the scattered light wave (angle θ) 38 generated by stationary particles, having a fixed phase, $\phi_{scat}$, the resulting light signal 44 will vary in intensity, possessing a periodic component having the same period as the voltage drive signal, $T_M$. For example, if the intensities of the scattered light wave 38 and the reference light wave 43 are the same (contrary to the usual desired condition), the intensity of the resulting light wave after coherent superposition will vary periodically from a maximum value (four times the intensity of either wave) to zero. The former value results from complete "constructive" interference of the two waves, when they have the same phase, while the latter value results from total "destructive" interference, when the phases of the two waves differ by π radians (180°). In a more typical case, with the intensity of the reference light wave roughly 10-20 times the intensity of the scattered wave, the resulting intensity after mixing will again vary periodically with time (period $T_M$). However, in this case the extent of variation of the intensity from maximum to minimum (now no longer zero), is much less than the 100% value obtained in the first example.

Figure 2A:
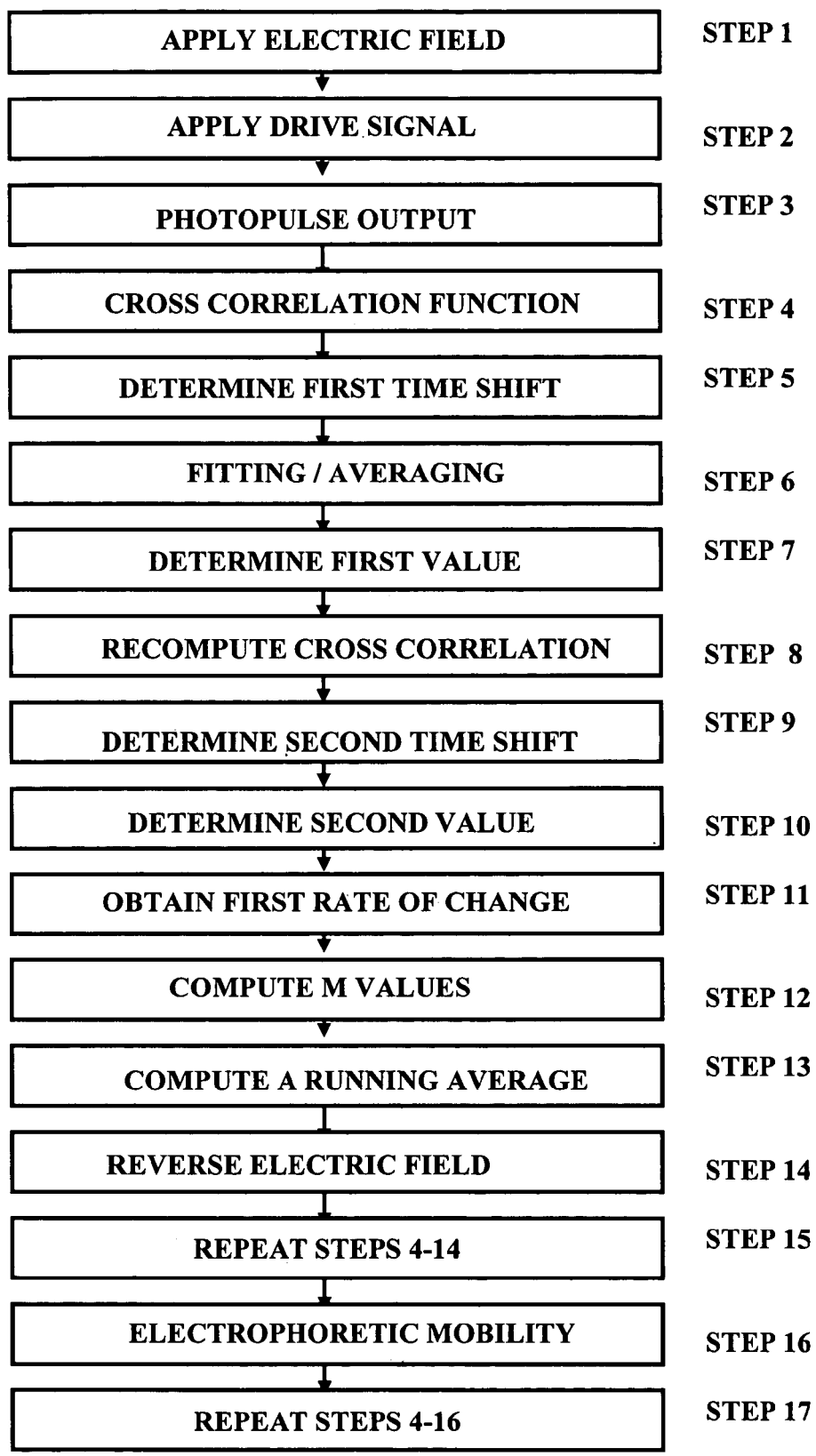
FIG. 2a shows an exemplary flowchart diagram for light scattering analysis using cross-correlation for phase shift analysis of an optical detection signal.

The operation of the apparatus (FIG. 1a), including a means, such as a cross correlator and related signal processor 46 used to implement the first embodiment, can be summarized using a simplified flow diagram, shown in FIG. 2a. The relevant processing steps comprising the analysis procedure, which can be stored as a computer program on a computer readable medium, and/or computer implemented, are exemplified below:

1. An alternating (square-wave) electric field of amplitude E and appropriate period $T_E$ (i.e., duration $T_E/2$ for each alternate field direction) is applied to the particle suspension;
2. A periodic linear-ramp ("sawtooth") voltage drive signal, $V_M(t)$, of appropriate period, $T_M$, resembling a rising "staircase" of N equally spaced steps in time ($\delta t$) and voltage ($\delta V_M$) is applied to the deflecting mirror modulator;
3. A photopulse output signal, I(t), representative of the detected light intensity signal (coherent superposition of the modulated reference light and scattered light waves) is directed to a cross-correlator means;
4. The cross correlation function (CCF), denoted by $C(\Delta t)$ =<I(t)×$V_M(t-\Delta t)$>, is constructed for N values of $\Delta t$, where N is the number of channels in the CCF, over a time $\Delta t_{CCF}$, typically an integral multiple, $M_{CCF}$, of period $T_M$;
5. A first value for the time shift, denoted by $\Delta t_1$, at which the peak, or maximum, value of the CCF occurs is determined;
6. Optionally a more accurate first value for $\Delta t_1$ associated with the maximum value of the CCF is determined from the CCF by use of one or more fitting and/or averaging procedures, resulting in improved peak time resolution;
7. A first value for the scattered light phase shift, $\Delta\phi_1$, corresponding to the first value for the time shift, $\Delta t_1$, is obtained;
8. The CCF is recomputed over the same time, $\Delta t_{CCF}$, after its contents are cleared;
9. A second value for the time shift, $\Delta t_2$, associated with the maximum value of the CCF is determined in the same manner, optionally using a fitting/averaging procedure to obtain improved resolution and accuracy;
10. A second value for the scattered light phase shift, $\Delta\phi_2$, corresponding to $\Delta t_2$, is obtained in the same manner;
11. A first value for the rate of change of the scattered light phase shift, $\Delta\phi/\Delta t|_1$, is obtained from $\Delta\phi/\Delta t|_1 = (\Delta\phi_2-\Delta\phi_1)/\Delta_{CCF}$;
12. M computational cycles, each similar to steps 8-11, are carried out, resulting in (M-1) values of the rate of change of the scattered light phase shift, where the (J-1)'th value is obtained from $\Delta\phi/\Delta t|_{J-1} = (\Delta\phi_J-\Delta\phi_{J-1})/\Delta t_{CCF}$;
13. A running average of the (M-1) successive calculated values of the rate of change of the phase shift, $\Delta\phi/\Delta t|_J$, for J=1, 2, ..., (M-1), is constructed and stored in computer memory on a continuous basis;
14. Following an elapsed time of $T_E/2$, the direction of the applied electric field is reversed. The computational cycles summarized in steps 4-13 are repeated for the next half-period, $T_E/2$, including a "grand" running average of the rate of change of phase shift values, constructed over both applied field directions (with reversed sign for the reversed-field half-period);

15. Steps 4-14 are repeated for the next full period, $T_E$, of the applied electric field, including the continuous grand running average of the rate of change of phase shift values;

16. After an appropriate elapsed time (typically measured in several seconds), the current grand running average value of the rate of change of phase shift, and corresponding value of electrophoretic mobility, μ, are stored in computer memory and displayed;

17. Steps 4-16 are repeated for the total desired elapsed time, or until the measured quantities are substantially stable and therefore reliable.

As indicated in FIG. 1b, the same optical configuration used to implement the first embodiment of this disclosure can also be used to measure the electrophoretic mobility, μ, and corresponding zeta potential, ζ, through a completely different analytical method, using a different means, such as a processing hardware 47 and associated computational procedures. For example, the digital signal processor can be switchable between the cross-correlation analysis 46 of the photopulse signal with the drive signal and an autocorrelation analysis 47 of the photopulse signal, for measuring the electrophoretic mobility of the sample based on a phase shift analysis or a frequency shift analysis. This alternative method incorporates certain aspects of related practices based on a measurement of the frequency shift, distinguished from the phase shift, in the detected-scattered light signal caused by the electric field-induced motion of suspended particles. Motion of the particles causes the frequency of the scattered light (again, detected at the scattering angle θ) to be Doppler shifted by an amount denoted by Δυ. This frequency shift, Δυ, depends not only on the magnitude of the particle velocity, but also its direction relative to the direction of the scattering wavevector, $\overline{K}$, which is rotated by angle θ/2 with respect to (i.e., "below") the x-axis. The desired electrophoretic mobility, μ, is proportional to Δυ and inversely proportional to the applied electric field strength, E, and the sine of the scattering angle, θ, $$\mu = (\lambda_o/n \sin \theta)(1/E) \Delta\upsilon. \quad (9)$$

In order to measure the frequency shift, Δυ, produced by the particle velocity, one can again utilize substantially the same optical "front end" apparatus that is used to measure the phase shift, Δφ, described earlier. A primary "reference" light wave 26 again gives rise to a secondary reference light wave 43 of reduced intensity, which again mixes coherently with the scattered light wave 38. A periodic "sawtooth" drive voltage, $V_M(t)$, of frequency $\upsilon_M$ (equal to $1/T_M$, where $T_M$ again denotes the period of the drive voltage waveform) is again applied to the deflecting mirror modulator means (e.g., piezoelectric transducer). The resulting detected light wave (representing a superposition of the reference and scattered light waves), having an intensity I(t), is again directed to a light detection means, such as a PMT detector. The resulting photopulse signal, proportional to I(t) and therefore also denoted by I(t) for convenience, is now analyzed using an autocorrelator means 47 (dashed-line path in FIG. 1b). The autocorrelator means 47 performs a very different mathematical function from that performed by the cross-correlator means 46 discussed above (solid-line path in FIGS. 1a and 1b). The autocorrelation function (ACF) effectively compares quantity I(t) with itself, shifted in time by Δt. The ACF is constructed by computing running sums of products I(t)×I(t−Δt) for a relatively large number (N) of discrete "channels" in time, Δt=0, δt, 2δt, . . . , (N-1)δt, using an optimal "channel width", δt (influenced by $\upsilon_M$).

In the hypothetical case in which the particles are stationary (i.e., no applied field and no diffusion), the resulting ACF includes a sinusoidal oscillation in time, Δt, having a characteristic frequency $\upsilon_M$, superimposed on a "baseline" level. When the particles move back and forth, in response to an applied alternating electric field, the frequency of the oscillating component of the ACF shifts to a new frequency, $\upsilon_M + \Delta\upsilon$, where Δυ is positive or negative, depending on the direction of particle motion relative to the direction of the applied field. (The polarity of the sawtooth drive voltage waveform is alternated whenever the applied electric field direction is reversed, in order to preserve the sign of Δυ for both field directions. Hence, the sign of Δυ depends on the polarity of the net charge on the particles.)

The characteristic frequency component, Δυ, proportional to the desired quantity, μ, can be extracted from the ACF using a fast Fourier transform (FFT) means, implemented, for example as a computer program that configures a computer. The resulting frequency power spectrum reveals a peak (in the case of a substantially single particle velocity, or mobility), having a position determined by the magnitude of Δυ and a width determined by the extent of random Brownian motion (and possibly convective drift) plus instrumental resolution. However, in practice the average values for μ, and therefore for ζ, obtained from the frequency shift method are limited in accuracy and resolution, especially in the case of relatively low particle velocities. In fact, in the case of especially low mobilities and/or very small electric fields (required for highly conducting samples) the frequency shift method can become insensitive to the resulting small particle velocities, becoming effectively useless for such applications. It is this limitation that can cause the phase shift method of analysis to be such an attractive alternative for electrophoretic mobility determination for low-velocity applications. However, the frequency shift method can remain useful (and preferable over the phase shift method) for applications in which there are two or more substantially different particle velocities, corresponding to two or more substantially different electrophoretic mobilities.

Given this brief discussion of the principles underlying the frequency-shift method of electrophoretic mobility determination, it is useful to summarize the frequency-shift mode of operation (dashed line) of the apparatus of FIG. 1b including autocorrelator 47 and associated signal processor. This operation is summarized using a simplified flow diagram, shown in FIG. 2b. The relevant processing steps comprising the analysis procedure, which can be stored as a computer program on a computer readable medium, and/or computer implemented, are exemplified below:

1. An alternating (square-wave) electric field of amplitude E and appropriate period $T_E$ (i.e., duration $T_E/2$ for each alternate field direction) is applied to the particle suspension;

2. A periodic linear-ramp ("sawtooth") voltage drive signal, $V_M(t)$, of appropriate period, $T_M$, resembling a rising "staircase" of N equally spaced steps in time (δt) and voltage ($\delta V_M$), is applied to the deflecting mirror modulator means;

3. A photopulse output signal, I(t), representative of the detected light intensity signal (coherent superposition of the modulated reference light and scattered light waves) is directed to an autocorrelator means;

4. The autocorrelation function (ACF), denoted by $A(\Delta t)=\langle I(t)\times I(t-\Delta t)\rangle$, is constructed continuously in time for N values of $\Delta t$, where N is the number of channels in the ACF;
5. A fast Fourier transform (FFT) of the ACF is constructed quasi-continuously in time using suitable hardware and/or software, thus yielding a frequency power spectrum of the detected light intensity, represented by the photopulse output signal, I(t);
6. Following an elapsed time of $T_E/2$, the direction of the applied electric field is reversed, and the polarity of the modulator voltage drive signal, $V_M(t)$, is also reversed, in order to compensate for the reversal in direction of the field-induced particle motion;
7. Computation of the ACF, without clearing its contents, and the FFT of the ACF, summarized in steps 4 and 5, respectively, continues, thus decreasing the influence of statistical fluctuations on the ACF and resulting FFT-generated frequency power spectrum;
8. Steps 4-7 are repeated for the next full period, $T_M$, of the applied electric field, including the quasi-continuous accumulation of data in the ACF, resulting in improved signal/noise ratio of the FFT-generated frequency spectrum;
9. After an appropriate elapsed time (typically measured in several seconds), the current FFT-generated frequency spectrum, the resulting average frequency shift, $\Delta\upsilon$, and the corresponding electrophoretic mobility, $\mu$, are stored in computer memory and displayed;
10. Steps 4-9 are repeated for the total desired elapsed time, or until the measured quantities are substantially stable and therefore reliable.

The technique of cross-correlation can be used to determine the time rate of change of the phase shift caused by motion of the suspended particles, due to an alternating applied electric field. The cross-correlation function (CCF), denoted by $C(\Delta t)$ and applied to the optical scheme shown in FIGS. 1a and 1b, can be expressed as $$C(\Delta t)=\langle I(t)\times V_M(t-\Delta t)\rangle. \tag{10}$$

I(t) represents the detected light intensity measured at time t, and $V_M(t-\Delta t)$ represents the voltage drive signal applied to the light deflecting modulator 25 at the earlier time, $t-\Delta t$, where $\Delta t$ is referred to hereinafter as the "time shift". The symbol $\langle\ \rangle$ represents a running summation of these products, $I\times V_M$, computed over a quasi-continuous series of t values, from the start to the end of data collection and processing. Implicit in Equation 10 is the fact that the indicated summation of products yields a single value for the cross-correlation function, $C(\Delta t)$, for each single value of time shift, $\Delta t$. The expression in Equation 10 yields an un-normalized CCF, which grows as the number of products included in $\langle\ \rangle$ grows—i.e., with increasing data collection and processing time. Alternatively, a normalized version of the CCF can be easily constructed, by dividing each computed value of $C(\Delta t)$ by the number of products (i.e., the number of discrete time values, t) used to construct $C(\Delta t)$.

Figure 3:
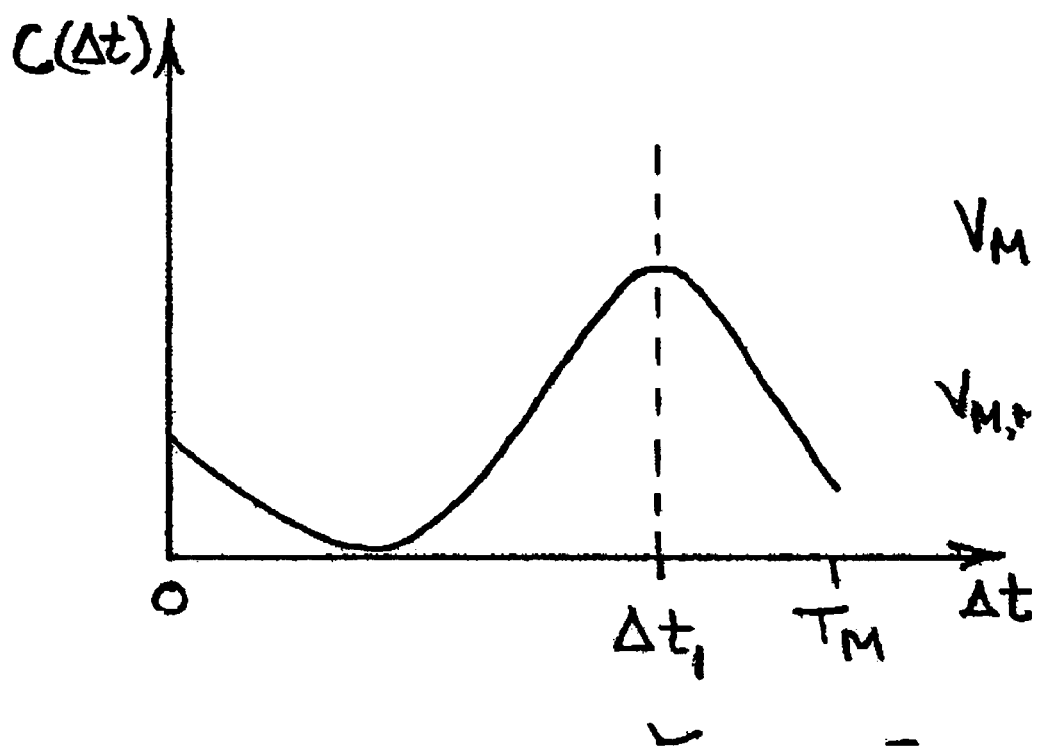
FIG. 3 shows an exemplary stylized plot approximating the shape of a cross-correlation result for an idealized, simplified cross-correlation.

FIG. 3 shows an exemplary stylized plot approximating the shape of the CCF that would be obtained for the idealized, simplified analysis case discussed above, in which the particles are assumed to be perfectly stationary. The important feature to be noted in this plot is the fact that there is a well-defined maximum value, or peak, in the CCF that occurs for a particular value of time shift, $\Delta t_1$, where $0\leq\Delta t_1\leq T_M$. This value of the time shift, $\Delta t_1$, corresponds to a particular modulator drive voltage, $V_M(\Delta t_1)$. This value, in turn, corresponds to a particular value of extension (or contraction), $\Delta S(V_M)$, of the piezoelectric transducer (PZT), which represents the distance of translation of the deflecting mirror 24. The relationship between $V_M$ and $\Delta S$ depends on the design of the PZT device. A typical PZT response characteristic, referred to herein as $R_{PZT}$, might be 15 microns per 100 Volts, or 0.15 μm/V (i.e., $R_{PZT}$=0.15 μm/V). Therefore, the distance of translation of the deflecting mirror 24 ideally varies linearly with time, from approximately zero to a maximum value $V_{M,MAX}\times R_{PZT}$, expressed in microns (μm). The extent of linear translation, $\Delta S(t)$, of the deflecting mirror 24 at a particular time, $\Delta t$, corresponding to a particular modulator drive voltage, $V_M(\Delta t)$, can therefore be expressed as $$\Delta S(\Delta t)=V_M(\Delta t)\times R_{PZT}. \tag{11a}$$

Equivalently (assuming a linear PZT response), $\Delta S(\Delta t)$ can be expressed in terms of the maximum modulator drive voltage, $V_{M,MAX}$, as $$\Delta S(\Delta t)=(\Delta t/T_M)\times V_{M,MAX}\times R_{PZT}. \tag{11b}$$

The translation at time $\Delta t$ of the deflecting mirror 24 by a given distance, $\Delta S(\Delta t)$, causes a shift in phase, $\Delta\phi(\Delta t)$, for the reference light wave 26, resulting in a new phase, equal to $\phi_{ref}+\Delta\phi(\Delta t)$. The magnitude of the phase shift, $|\Delta\phi(\Delta t)|$, depends on the extent of change in the OPL of the reference light beam, as discussed earlier. In one simple case, if the OPL changes by exactly one wavelength, $\lambda_o$, the phase changes by $2\pi$ radians (360°), equivalent to no change in phase at all. The same is true for any integer multiple of the wavelength. On the other hand, if the OPL changes by one-half the wavelength, $\lambda_o/2$ the phase of the reference light wave changes by $\pi$ radians (180°). The change in the OPL is limited, of course, by the maximum distance of translation of the deflecting mirror, equal to $V_{M,MAX}\times R_{PZT}$ (Equation 11a). However, it also depends on the angular geometry of the reference beam path shown in FIGS. 1a and 1b. Specifically, the change in the OPL depends on the angle between the first "leg" of the reference light beam 23, connecting the beam splitter 22 (point "A") to the light deflector 24 (point "B"), and the second leg 26, connecting the latter to the light diffuser means 27 (point "C"). This angle affects the change in the phase of the reference light wave caused by a given distance of translation, $\Delta S$, of the deflecting mirror 24. In one hypothetical example, where this angle approaches zero (not feasible, given the optical design shown in FIGS. 1a and 1b), the phase is changed by the maximum amount for a given translation, $\Delta S$, for example equaling $\pi$ radians if $\Delta S=\lambda_o/4$. In another hypothetical example, where the angle approaches 180°, there is essentially no change in the phase, regardless of the magnitude of $\Delta S$.

It is therefore convenient to employ a calibration constant, referred to hereinafter as $P_o$, having the units of radians/μm. This constant establishes the change in phase, $\Delta\phi$, of the reference light wave associated with a given distance of translation of the deflecting mirror means, $\Delta S$, for the particular optical geometry employed, $$\Delta\phi=P_o\times\Delta S. \tag{12}$$

The various parameters defined and discussed above, can be used to convert the time shift, $\Delta t_1$, corresponding to the maximum (peak) value found for the calculated CCF, to the desired phase shift, $\Delta\phi_1$, of the reference light wave. From Equations 12 and 11b, a relationship can be established as follows:

$$\Delta\phi_1=\Delta\phi(\Delta t_1)=P_o\times(\Delta t_1/T_M)\times V_{M,MAX}\times R_{PZT}. \tag{13}$$

The value of $\Delta\phi_1$, or $\Delta\phi(\Delta t_1)$, is the amount of phase shift, ranging from 0 to ±2π radians (360°), applied to the reference light wave (by the deflecting mirror means) which causes its resulting phase, $\phi_{ref}+\Delta\phi(\Delta t_1)$, to be the same as the phase of the scattered light wave (when they are superposed), whatever that happens to be. The maximum modulator drive voltage, $V_{M,MAX}$, and piezoelectric transducer response, $R_{PZT}$, can be such that a phase shift of at least 2π radians for the reference light wave can be obtained at the maximum drive voltage. From Equation 13, this requirement, which is achieved for the largest extension (or contraction) of the modulator means, at $\Delta t_1=T_M$, becomes equivalent to the condition, $$P_o \times V_{M,MAX} \times R_{PZT} Z \geq 2\pi \text{(radians)}. \qquad (14)$$

In practice, an exemplary system can be configured so that the deflected light modulator means 25 is able to effect a total phase shift (i.e., from $V_M=0$ to $V_M=V_{M,MAX}$) somewhat larger than the maximum value of 2π radians that is needed—e.g., 105% to 110% of this value. This condition assumes that the light deflection modulator means 25 is configured to effect mirror translation in only one direction (either an extension or a contraction, depending on the chosen polarity of the driver voltage, $V_M$). Alternatively, if the light deflection modulator 25 is able to effect mirror translation in both directions, then the maximum phase shift that is applied (in either direction) to the reference light wave can be only half as large—i.e., ±π radians, with Equation 14 modified accordingly.

Figure 4:
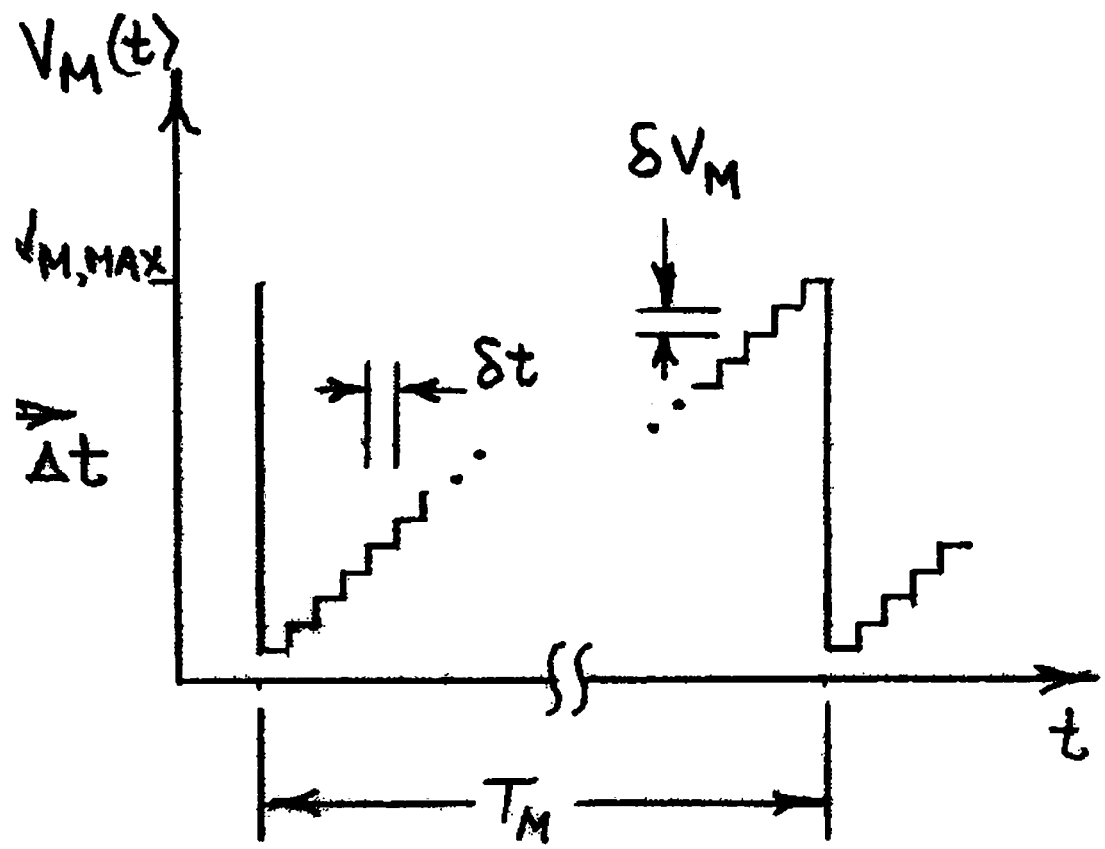
FIG. 4 shows an exemplary digital voltage waveform to drive a light deflection modulator means.

The CCF can be used to determine the phase shift (and time rate of phase shift) in the detected scattered light wave that results from translation of the charged, suspended particles due to application of an electric field. The use of the CCF for this particular application is greatly facilitated by manipulating all relevant signals and computed quantities using digital, rather than analog, techniques and technologies. This can simplify and improve the associated apparatus, given the availability of digital signal processing (DSP) 46 technology and other integrated circuit means. This digital-based approach in practice can also result in improved stability (e.g., immunity against long-term voltage drifts), better reliability and higher accuracy of the resulting measured quantities of interest With the above considerations in mind, a digital version of the periodic sawtooth voltage waveform needed to drive a means, such as a light deflecting modulator 25, which can be a piezoelectric translator means, is constructed, or synthesized. FIG. 4 shows an expanded portion of the resulting digitally constructed waveform, in which the increasing ramp voltage consists of a sequence of uniform, incremental steps in voltage, thus forming a rising "staircase" waveform. The number of steps comprising the staircase waveform is denoted by N, where it is preferable to use a standard binary format, i.e., $N=2^n$, with typical values of n being 6, 7, 8 (or higher), resulting in values of N equal to 64, 128, 256 (or higher), respectively. This binary format is very convenient, given the ease of constructing the staircase waveform using a simple binary digital counter integrated circuit. For example, a highly stable, continuous square-wave digital signal can be obtained from the crystal controlled digital clock that controls the timing of the digital processor used to construct the CCF. The master square-wave signal can be divided down in frequency, if necessary, to reach the desired frequency for clocking the binary counter integrated circuit, yielding the desired number of voltage steps per unit of time. The binary output is fed into a digital-to-analog (D/A) converter circuit, the output of which is the desired staircase modulator voltage signal (apart from the possible need to adjust the maximum voltage, $V_{M,MAX}$, using a suitable operational amplifier circuit to condition the output voltage of the D/A circuit). When the desired maximum number of steps per cycle (N) is reached, the associated electronic circuit can be designed to clear the contents of the binary counter. The conditioned output of the D/A circuit, i.e., voltage signal $V_M$, will be returned to zero (or some minimum starting voltage), at which time the process of building up the staircase waveform is repeated.

The N steps used to construct the modulator drive signal, $V_M(t)$, effectively determines the phase resolution of the phase shift measurement, in the absence of analytical techniques designed to improve the resolution (described below). The smallest increment in modulator drive voltage, denoted by $\delta V_M$, equals the maximum voltage applied to the modulator means divided by the number of steps, $$\delta V_M = V_{M,MAX}/N. \qquad (15)$$

This minimum increment in modulator drive voltage in turn yields a minimum increment in translation, δS, of the deflecting mirror, given by Equation 11a, $$\delta S = \delta V_M \times R_{PZT}. \qquad (16)$$

This minimum increment in mirror translation in turn gives rise to a minimum increment in the phase shift of the reference light wave, δφ, given by Equation 12, $$\delta\phi = \delta V_M \times P_o \times R_{PZT}. \qquad (17)$$

Similarly, there is a minimum increment in time, denoted by δt, associated with the digitally constructed sawtooth drive voltage waveform, which simply equals the period of the waveform, $T_M$, divided by the number of steps, $$\Delta t = T_M/N. \qquad (18)$$

This minimum increment in time, δt, effectively establishes the time resolution of the phase shift measurement, based on cross-correlation of the net detected intensity, I(t), with the modulator driving voltage, $V_M(t)$. Because the phase of the reference light wave is incremented (by δφ) to a new value only after a time increment equal to δt, there is no sense in computing the value of C(Δt) for successive intervals of time smaller than δt. Hence, this small element of time becomes the "channel width" used to construct the CCF (Equation 10). Quantity C(Δt) is computed at the discrete times Δt=0, δt, 2δt, 3δt, . . . , (X-1)δt, where X is the number of channels used to construct a digital representation of the CCF. Given the periodicity of the modulator drive voltage waveform, the number of steps, N, used to construct the staircase waveform is conveniently chosen to be the number of channels used to construct the CCF—i.e., X=N.

A numerical example is useful: channel width δt=20 μsec and N=64 channels. These choices imply a modulation period, $T_M$, of 64×20 μsec=1.28 msec for the periodic sawtooth drive signal, equivalent to a frequency, $\upsilon_M$, of $1/T_M$=781.25 Hz. This is an acceptable frequency, given the fact that a piezoelectric transducer of appropriate design typically operates efficiently at frequencies ranging from less than 100 Hz up to several kHz. The assumed values for parameters N and δt imply that 64 different products of I(t) and $V_M(t-\Delta t)$ must be computed for Δt=0, δt, 2δt, . . . , 63δt during each successive time interval of 20 μsec, requiring a relatively fast digital processor. During this time interval these 64 new products must be added to the contents of their respective channels, representing the running sums of previously computed products comprising the CCF. During the next time interval of 20 μsec, this same process is repeated, with the CCF channel contents again updated. This procedure continues for increasing values of time, t, in increments of δt, for an elapsed time chosen to optimize the accuracy and stability (i.e., reproducibility) of the electrophoretic mobility measurement.

Calculation of the CCF is straightforward, given the digital nature of the two signals that are cross-correlated. The detected intensity signal, I(t), typically already exists in a form that is amenable to digital manipulation. Assuming that a PMT detector 41 is used to detect the coherently superposed scattered and reference light waves, its output signal 45, after suitable conditioning (discrimination and amplification), consists of individual photopulses, easily converted to pulses of uniform amplitude, compatible with digital integrated circuits. This output 45 therefore already comprises a digital representation of the intensity—i.e. the number of pulses per unit time. Therefore, the quantity I(t) in the definition of C(Δt), in Equation 10, simply equals the number of detected photopulses that occur in the "current" time channel, during a time interval of width δt. This number is easily obtained using a well-known digital counter integrated circuit.

The second signal used for construction of the CCF is the modulator driving voltage, $V_M$, where the N values are taken at times shifted from the current time by Δt—i.e., shifted by 0 to 63δt. This is a trivial task, given the fact that $V_M(t)$ has been constructed in simple staircase fashion, with uniform voltage increments, $\delta V_M$, of $V_{M,MAX}/N$, from one time interval (δt) to the next. The voltage for the first time interval is $\delta V_M$, that for the second interval is $2\delta V_M$, and so forth, up to and including $64\delta V_M$. All of these voltage values possess a common, constant factor, $\delta V_M$, which ultimately affects only the magnitude of the resulting CCF, but not its shape. Therefore, the values of $V_M(t-\Delta t)$ needed to compute the CCF consist simply of the sequence of integers, 1, 2, 3, ..., N, where N is the number of channels (and steps in the sawtooth voltage waveform), i.e., 64 in the example above. Consequently, it becomes a simple, fast digital processing procedure to obtain the N separate products needed to update the contents of the N channels of the CCF. These products are simply I(t), 2I(t), 3I(t), . . . NI(t), where I(t) consists of the number of detected intensity photopulses that are counted at the "current" time, t—i.e., during the time interval δt, equal to the channel width.

The minimum length of time over which the CCF is constructed is equal to the period of the modulator drive voltage signal, $T_M$, which equals N×δt, or 1.28 msec for the example discussed above. If there were no statistical fluctuations or other sources of "noise" present, there would be no purpose served in collecting light intensity data and computing the CCF for any time longer than $T_M$, given the perfectly repetitive, periodic nature of the voltage waveform, $V_M(t)$, that drives the piezoelectric transducer means. Each of the N discrete values of the drive voltage, $V_M$, gives rise to a corresponding discrete amount of phase shift that is applied to the reference light wave before it mixes with the scattered light wave. In the simplified case in which the maximum mirror translation (produced by the maximum drive voltage, $V_{M,MAX}$) gives rise to a reference wave phase shift of 2π radians, then each of the N successive increments in mirror translation yields an incremental phase shift of 2π/N radians, or 5.625° for the example of N=64. The resulting digitized form of the CCF would thus possess a time resolution of δt=20 μsec and a corresponding phase shift resolution of 5.625°. If the particles giving rise to the scattered light wave move sufficiently to shift the phase of the scattered wave by this amount, then the peak value of the CCF will shift in time by one "channel", i.e., by δt=20 μsec. The shift in the CCF peak will represent either an increase or decrease in phase, depending on whether the particle has moved in the positive or negative x direction. The amount of particle translation needed to produce this phase shift (Equation 4b) is Δx=0.031 μm, assuming $\lambda_o$=0.635 μm, n=1.33 and θ=14°.

In practice, there are sources of "noise" that can affect the quality (signal/noise ratio) of the computed CCF and resulting derived quantities, Δϕ and Δϕ/Δt. Instrument-related sources of noise include the laser light source 20, non-linearity (including "jitter") of the piezoelectric transducer 25 and analog electronic noise associated with the PMT detector 41 (including discriminator and preamplifier) and various power supplies. There are also significant sources of "noise" inherent in the sample contained in the cuvette 33. Fluctuations in the scattered light intensity are produced by contaminants in the sample suspension, including dirt, air bubbles and particle agglomerates, which drift in and out of the incident laser light beam 32. The influence of these noise sources can be reduced to an acceptable extent by filtering or centrifuging the sample suspension or otherwise improving the sample preparation procedure.

There are also random fluctuations in the positions of the suspended particles that can occur, due to Brownian motion, or diffusion. The magnitude of the diffusivity of the particles is inversely proportional to their size, as described by the well-known Stokes-Einstein relation. The positions of the particles fluctuate in random-walk fashion along all three axes, which results in random fluctuations in the phase of the scattered light at any scattering angle. These fluctuations in position are superimposed on the simple linear translation (along the x-axis) that is induced by the applied electric field using the electrodes 34 and 35. In the case of small particles that either are exposed to a relatively small electric field or which happen to possess a small electrophoretic mobility, the extent of motion associated with random Brownian motion may actually substantially exceed the linear motion that is induced by the applied field. In such cases, it is particularly important that the new technique for measuring the electrophoretic mobility be able to mitigate the influence of this unavoidable, random source of "phase noise", so that it does not substantially affect the accuracy or reliability of the phase shift measurement. This can be an advantage of the CCF technique and associated procedures as disclosed.

There is another source of noise, potentially both systematic and random, that can result in errors in the measured phase shift. First, small gradients in temperature can exist within the sample cuvette 33 (e.g., across opposite or adjacent surfaces), due to limitations in the design of the sample cell holder and associated temperature regulator. As a result of these temperature differences, convection will exist within the sample cuvette 33 to one extent or another, causing the suspended particles to drift slowly in one direction or another, either indefinitely or over a substantial period of time. This motion is uncorrelated with the intended translational motion of the particles induced by the applied electric field. The velocity associated with this convective fluid flow may be comparable to, or even substantially exceed, the particle velocity caused by the applied electric field. Hence, the signal analysis technique can cancel or substantially reduce the spurious contributions to the measured rate of change of phase shift caused by this common effect. In addition, in cases where there is a significant electrical current created by the applied electric field, due to the presence of significant amounts of conducting ions in the suspension, the resulting Joule heating may produce random convective fluid flow. It is also useful if the signal analysis technique can reduce the additional, random phase shifts caused by this current-induced convective fluid flow, generally uncorrelated with the magnitude and direction of the applied electric field.

With the foregoing introductory description, the phase analysis measurement procedure is summarized. First, in order to improve the signal/noise ratio of the computed CCF and thereby mitigate the effects of random noise sources (e.g., instrument-related, as well as Brownian motion), it is useful to construct the CCF over several periods, $T_M$, of the periodic modulator drive voltage, $V_M(t)$, rather than just one period, as discussed earlier. As a result, the statistical fluctuations in the contents of the various channels comprising the CCF will be reduced. As an example, the CCF might be constructed over an elapsed time, denoted by $\Delta t_{CCF}$, equal to five cycles of the periodic modulator drive voltage, resulting in a total cross-correlation time of 5×1.28 msec, or 6.4 msec, using the earlier parameter values, $\delta t=20$ μsec and $N=64$. After this time has elapsed, the time shift, $\Delta t_1$, corresponding to the peak value of this "first" CCF, denoted by $CCF_1$, is determined. This value of $\Delta t_1$ implies a shift in the scattered wave phase, $\Delta\phi_1$, given by $$\Delta\phi_1 = (\Delta t_1/T_m) \times \Delta\Phi. \quad (19)$$

Quantity $\Delta\Phi$ is the known, predetermined change in the phase of the reference light wave produced by the maximum modulator drive voltage, $V_{M,MAX}$. As discussed earlier, the value of $\Delta\Phi$ must at least equal $2\pi$ radians, and preferably it is 5 to 10% larger than this value. In any case, it has a fixed, known value.

From the discussion above, it would appear that the resolution of this measured time shift value is limited by the chosen parameter N, i.e., the number of steps in the periodic modulator drive voltage waveform, or the number of channels in the CCF. Hence, it would seem that the resolution in the measured time shift, $\Delta t_1$, is equal to the channel width, $\delta t$, and therefore the resolution of the calculated corresponding phase shift, $\Delta\phi_1$, would appear to equal $\Delta\Phi/N$, or $2\pi/64=5.625°$ in the case of $\Delta\Phi=2\pi$ radians and $N=64$, as noted earlier.

However, the resolution in the measured time shift associated with the peak in the CCF can be made substantially better (smaller) than what is indicated above. Each computed CCF result can include a discrete plot composed of N points, or values, separated equally along the time axis. However, each successive computed CCF result can be expected to show changes, albeit perhaps relatively small, in many, if not most, of the N values, compared to the previous CCF result, even if there is no discernable change in the position ($\Delta t_1$) of the peak of the CCF. Therefore, an appropriate curve-fitting/averaging technique can be used to obtain a smoothed, quasi-continuous version of the original, digitized version of the computed CCF. Through the use of such a procedure, a higher-resolution definition of the "peak" of the computed CCF can be obtained. In this way, one can obtain a higher resolution, and therefor more accurate, value of the time shift, $\Delta t_1$, corresponding to the peak of the CCF, thus yielding a more accurate value for the phase shift, $\Delta\phi_1$, of the scattered light wave.

The next step is to clear the digital contents of the CCF and repeat the measurement for the same elapsed time, $\Delta t_{CCF}$—i.e., 6.4 μsec, assuming the same parameter example as before. This second measurement, including optimized curve-fitting/averaging after cross correlation, yields a new value for the time shift for the peak of the "second" CCF, denoted by $\Delta t_2$, which, through Equation 19, yields a new value for the phase shift, denoted by $\Delta\phi_2$. Given these first two measured values of the phase shift, it is now possible to obtain a first value for the rate of change of the phase shift of the scattered wave, denoted by $\Delta\phi/\Delta t|_1$, $$\Delta\phi/\Delta t|_1 = (\Delta\phi_2 - \Delta\phi_1)/\Delta t_{CCF}. \quad (20)$$

where $\Delta t_{CCF}$ equals the time between successive phase-shift determinations, e.g., 6.4 msec using the same parameter example as before.

This same procedure can be repeated a multiple number of times, denoted by M, where after each measurement cycle a new value for the rate of change of the phase shift is obtained. For example, following the J'th cycle, the new rate of change of the phase shift is given by, $$\Delta\phi/\Delta t|_{J-1} = (\Delta\phi_J - \Delta\phi_{J-1})/\Delta t_{CCF}. \quad (21)$$

In the absence of any of the noise/fluctuation sources discussed above, each of the values of the rate of change of the phase shift determined by the procedure described above would be the same, in which case there would have been no need to determine more than one value. However, one can expect fluctuations in these values, from one to the next, because of the influence exerted by the various "noise" sources always expected to exist. This can be the case for the random fluctuations in the positions of the particles that give rise to the detected scattered light wave, due to Brownian motion, or diffusion. This basic physical effect is universally present, making its consequences for the phase analysis unavoidable. The smaller the particles, the greater the consequences of this effect.

Therefore, this exemplary embodiment encompasses an additional procedure for determining electrophoretic mobilities by phase shift analysis. Namely, the desired rate of change of the scattered light phase shift, $\Delta\phi/\Delta t$, is constructed as a running average of each of the individual values, $\Delta\phi/\Delta t|_J$, for J=1, 2, 3, ..., M-1, that are computed after each elapsed time interval, $\Delta t_{CCF}$, described above. This procedure serves the function of substantially canceling over time the random fluctuations that occur for each of the individually measured phase shifts, $\Delta\phi_J$, and therefore also for each of the subsequent rates of change of the phase shifts, $\Delta\phi/\Delta t|_J$, due principally to Brownian motion of the particles. The "noise" caused by Brownian motion, and other noise sources, can result in both increases and decreases in the individually measured values of $\Delta\phi_J$. The optimal choice of elapsed time $\Delta t_{CCF}$ for the sequence of CCF determinations—i.e., for the number of measurement cycles, M—can be established experimentally, using samples of interest, measured under typical operating conditions. A reasonable choice for the number of measurement cycles used for the averaging process, assuming the same parameter example used above, might be M=25. As a result, the total elapsed time for completion of the measurement cycles becomes 25×6.4 msec, or 0.16 sec. Following this averaging procedure, an optimized value for the quantity $\Delta\phi/\Delta t$ will have been obtained, thus yielding a value for the electrophoretic mobility, μ, from Equation 8.

Next, the direction of the applied electric field is reversed, simply accomplished by reversing the polarity of the voltage, V, applied to the electrodes that are immersed into the particle suspension. (The magnitude of the electric field, E, is equal to the applied voltage, V, divided by the distance between the opposing surfaces of the electrodes.) Hence, if the electric field vector, $\overline{E}$, was first pointing in the positive x-axis direction, it is now switched to point in the negative x-axis direction. As with other existing ELS-based techniques, it is necessary to periodically reverse the applied electric field in order to avoid long-term electrolysis, or electroplating, effects, i.e., causing the charged particles and other charged components contained in the suspension to be attached to the oppositely charged surfaces of the electrodes.

Following reversal of the electric field direction, the same measurement procedure described above is repeated, i.e., M consecutive measurements of $\Delta\phi_J$, for J=1, 2, 3, ..., M, for equal elapsed cross-correlation times, $\Delta t_{CCF}$, and M-1 resulting determinations of $\Delta\phi/\Delta t|_J$, for J=1, 2, 3, ..., M-1. A running average of the latter quantities then yields, after a second total elapsed time of $M \times \Delta t_{CCF}$, a second optimized value for the quantity, $\Delta\phi/\Delta t$. This result is then averaged with the result obtained from the first sequence of measurements, thus beginning the formation of a "grand" running average of the sequentially determined values for $\Delta\phi/\Delta t$ obtained for each alternating cycle (including both polarities) of the applied electric field. This grand averaging process is continued for as long a time as desired, or necessary, in order to obtain results that are stable (substantially constant) and hopefully reproducible. However, the sign of the resulting measured phase shift (and rate of change of phase shift) values must be reversed for each of the alternate measurement cycles (i.e., the $2^{nd}$, $4^{th}$, $6^{th}$, etc.), in order to compensate for the fact that the electric field is reversed in direction in those alternate cycles. Hence, the resulting phase shift values for each measurement cycle will always be (on average, apart from fluctuations) either positive or negative, regardless of the direction of the applied electric field during that cycle. Ultimately, the grand running average of the rate of change of phase shift values, $\Delta\phi/\Delta t$, and corresponding average $\mu$ values, will either have a positive or negative sign, designed to be the same as the sign of the charge carried by the particles. Therefore, the CCF-based analysis technique yields not only the magnitude of the desired electrophoretic mobility, $\mu$, but also its polarity (sign).

There is an exemplary benefit that automatically accrues to the above described technique of constructing a "grand" running average of measured $\Delta\phi/\Delta t$ values, performed over alternating electric field polarities. As discussed earlier, the suspended particles are often caused to drift in position along one direction or another, or over rapidly changing directions, due to the existence of convection currents of varying strength caused by thermal gradients within the sample cuvette 33. The resulting direction of particle motion due to convective flow is generally uncorrelated with the direction of translation established by the polarity of the applied electric field. Therefore, the fact that there is a grand running average of the measured value of $\Delta\phi/\Delta t$ over alternating electric field directions means that any shift in the resulting answer for the mobility, $\mu$ that would otherwise occur due to unidirectional particle motion caused by convective flow may therefore be largely canceled.

In cases where the applied electric field is relatively large (e.g., $E \geq 10$ V/cm) and the particle mobility is also relatively large (e.g., $\mu \geq 2$ M.U.), the resulting electrophoretic velocity, v, will therefore also be relatively large (e.g., $v \geq 20$ $\mu$m/sec). This velocity will therefore likely exceed considerably the additional velocity imposed by background convection currents (assuming the temperature is relatively constant and uniform everywhere in the sample cuvette). In that event, if the grand averaging of $\Delta\phi/\Delta t$ over alternating electric field directions were not employed, the relative errors in the reported values for $\mu$ could be expected to be small and therefore tolerable. However, in cases where the applied field strength is much lower (e.g., $E \leq 1$ V/cm), required to avoid excessive Joule heating in the presence of significant sample conductivity, and perhaps the particle mobility is also small (e.g., $\mu \leq 1$ M.U.), the resulting errors may be unacceptable. In this case, the stray background convection currents will result in particle velocities that are likely comparable to, if not greater than, the velocity caused by the applied electric field. The resulting error in the reported value for $\mu$, in the absence of the grand averaging technique, may prove to be too large, resulting in results that are grossly inaccurate and also non-reproducible, given the unpredictability of the convective flow over time.

Notwithstanding the definition of the CCF given in Equation 10 and the related description above of the measurement process, the roles of the quantities I(t) and $V_M(t-\Delta t)$ that are used to obtain the CCF can be reversed. That is, C($\Delta t$) can be defined equally effectively in terms of $I(t-\Delta t)$ and $V_M(t)$. In this case, the value for the modulator drive voltage, $V_M$, at the "present" time, t, is multiplied by the digitized intensity, I, at the shifted time, $t-\Delta t$, for a particular value of $\Delta t$. As before, the CCF is computed over an elapsed time $\Delta t_{CCF}$. Such products are then added together in a running sum over successive times separated by the channel width, $\delta t$, in order to obtain the object of interest, C($\Delta t$). The result of the cross correlation operation remains the same—i.e., the determination of the phase shift, $\Delta\phi$, and rate of change of the phase shift, $\Delta\phi/\Delta t$, between the reference light beam and the (phase-shifted) scattered light wave.

The power of the ELS measurement of electrophoretic mobilities based on phase shift analysis using the new cross correlation technique with associated averaging of results over alternating electric field directions, as described herein, can best be appreciated by reviewing some typical analysis results. A series of measurements were made of the electrophoretic mobility, $\mu$, as a function of elapsed time, for various applied E field values, for an aqueous suspension of uniform polystyrene latex particles of diameter 491 nm. The concentrated latex particles (Duke Scientific, Palo Alto, Calif., Cat. # 3495A) were diluted 500:1 in water, adjusted to pH 10 (added KOH) and containing 0.001M KCl, in order to meet the criterion of non-overlapping electrical double layers required for the Smoluchowski approximation. The direction of the applied electric field between the electrodes 34 and 35 was reversed after each 0.16-sec interval, resulting in a period of 0.32 sec, or a frequency of approximately 3 Hz. A grand averaging of individual measured $\Delta\phi/\Delta t$ values, and corresponding $\mu$ values, as discussed above, was performed continuously, and the resulting values of $\Delta\phi/\Delta t$ and $\mu$ were plotted and stored every 9 sec for the duration of the analysis process. In the case of relatively large applied fields—i.e., E=5 or 10 V/cm—the results typically became stable after less than 30 seconds, remaining essentially constant thereafter. However, at much weaker applied fields—i.e., $E \leq 1$ V/cm—a longer time, typically 2-3 min, can be used for the results to become substantially constant.

Figure 5A:
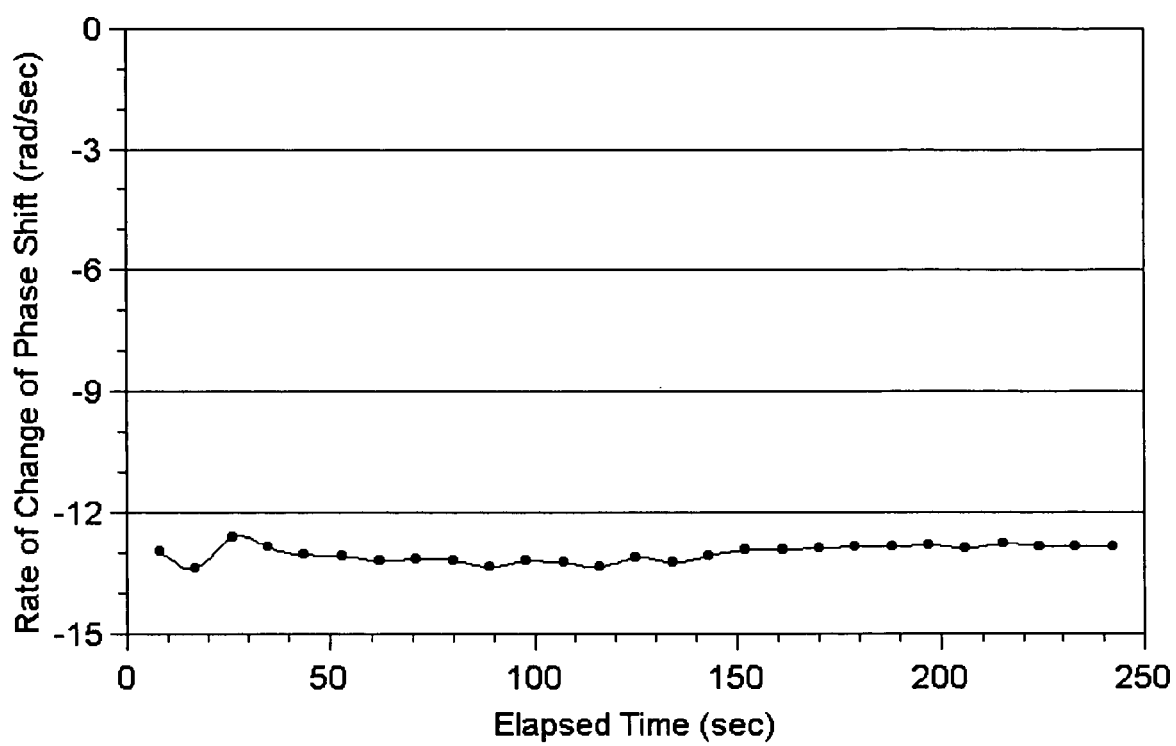
FIG. 5a shows an exemplary plot of time history of the measured rate of change of the phase shift values for the electric field strength of 1 V/cm.
Figure 5B:
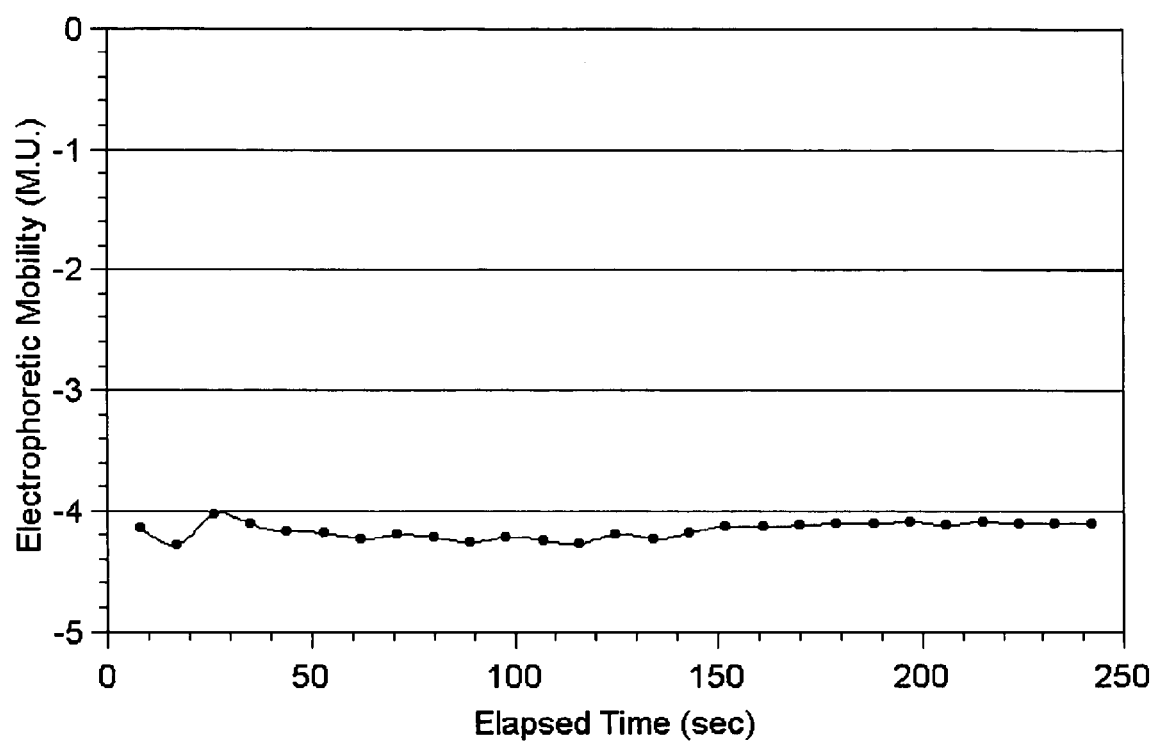
FIG. 5b shows an exemplary plot of time history of the corresponding electrophoretic mobility values for the electric field strength of 1 V/cm.
Figure 5C:
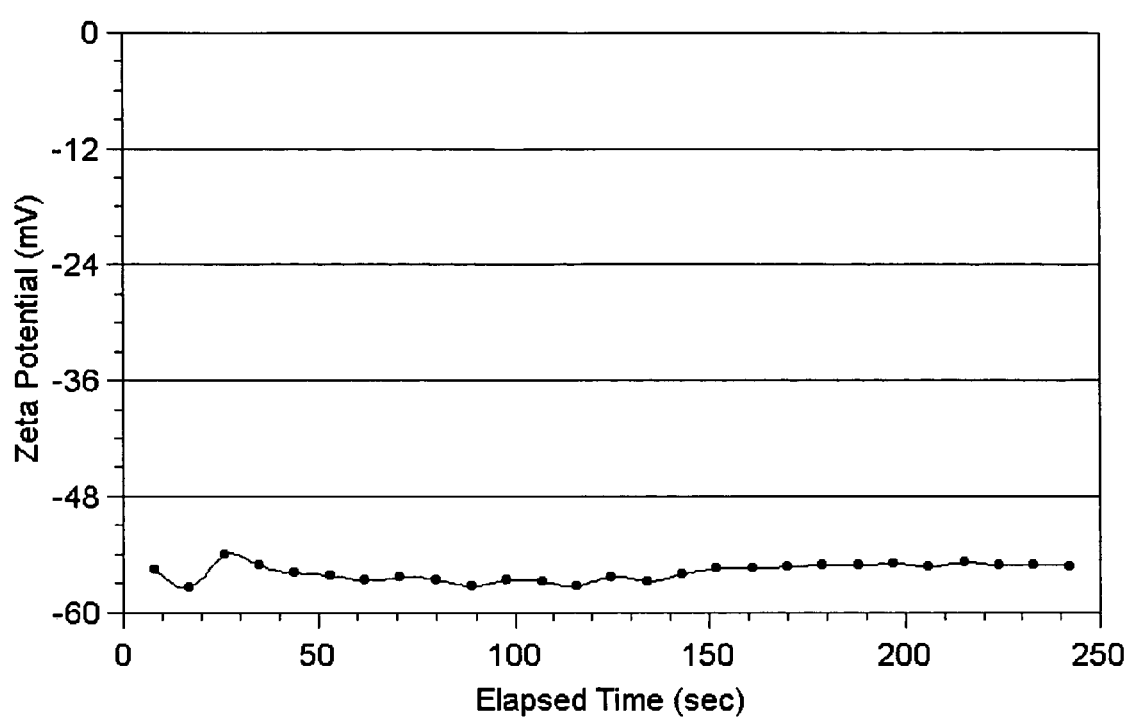
FIG. 5c shows an exemplary plot of time history of the corresponding zeta potential values for the electric field strength of 1 V/cm.

FIG. 5a shows an exemplary expanded plot of the measured rate of change of the phase shift, $\Delta\phi/\Delta t$, vs. elapsed time for E=1 V/cm. As seen, the fluctuations in the value became substantially constant after about 150 sec of data collection and grand averaging. FIG. 5b shows a plot of the time history of the corresponding electrophoretic mobility values, $\mu$, proportional to the measured values of $\Delta\phi/\Delta t$ (FIG. 5a), obtained from the latter using Equation 8. FIG. 5c shows an exemplary plot of the time history of the zeta potential values, $\zeta$, corresponding to the values of $\mu$ (FIG. 5b), using the Smoluchowski approximation, $\zeta = (\eta/\epsilon)\mu$, with $\eta = 0.933$ cP and $\epsilon = 78$ (23-deg C.). After an elapsed time of 150 sec, the exemplary results (with the minus sign indicating negatively charged particles) were, $\Delta\phi/\Delta t = -12.94$ rad/sec; $\mu = -4.13$ M.U.; and $\zeta = -55.48$ mV.

An exemplary plot of the time history of the zeta potential, $\zeta$, for the same sample, but with five times the applied electric field strength, E=5 V/cm, would indicate substantial settling of the result after about 45 sec of data collection and averaging, resulting in, $\Delta\phi/\Delta t = -64.22$ rad/sec; $\mu = -4.10$ M.U.; and $\zeta = -55.08$ mV.

As expected, the value obtained for $\Delta\phi/\Delta t$ was close to five times that found for E=1 V/cm. The results for $\mu$ and $\zeta$ were very close to those obtained at the lower E value.

Given the time history of $\zeta$ for the same sample, but with a further factor of two increase in the electric field strength, to E=10 V/cm, a plot would indicate that even less data collection and averaging (35 sec) are now needed to achieve substantial settling of the result, $\Delta\phi/\Delta t = -129.27$ rad/sec; $\mu = -4.05$ M.U.; and $\zeta = -54.35$ mV.

As expected, the value obtained for $\Delta\phi/\Delta t$ was close to twice that found for E=5 V/cm and 10 times that found for E=1 V/cm. Again, the results for $\mu$ and $\zeta$ were very close to those obtained at the lower E values.

It is instructive to review the extent of particle translation, $\Delta x$, that occurs during application of the electric field in one direction, i.e., for a total elapsed time $\Delta t=0.16$ sec. The resulting values of $\Delta x$ for representative values of $\mu$ and E are listed in Table 1. For small $\mu$ and/or E, an exemplary maximum particle translation due to the applied electric field may be substantially smaller than its diameter.

These values of $\Delta x$ can be compared with values of the root mean square displacement of the particles due to random diffusion (Brownian motion), denoted by $\Delta x_D$, given by $$\Delta x = (2D\Delta t)^{1/2}. \quad (22)$$

The diffusivity, D, is given by the familiar Stokes-Einstein relation, $$D = kT/3\pi\eta d, \quad (23)$$

where k is Boltzmann's constant, T the temperature (° K.), $\eta$ the viscosity and d the particle diameter. Representative results (for water at 23-deg C.) are shown in Table 2. For small particles, the random motion (on average) due to Brownian motion may substantially exceed the translation due to the applied electric field. This fact highlights the value of the cross correlation procedure in extracting the desired, possibly very small, particle movement from the "noise" associated with undesirable, possibly much larger, particle motion due to random diffusion.

TABLE 1

| $\mu$ (M.U.) | E (V/cm) | v ($\mu$m/sec) | $\Delta x$ ($\mu$m) |
|---|---|---|---|
| 0.5 | 1 | 0.5 | 0.08 |
| 0.5 | 2 | 1 | 0.16 |
| 0.5 | 5 | 2.5 | 0.4 |
| 0.5 | 10 | 5 | 0.8 |
| 1 | 1 | 1 | 0.16 |
| 1 | 2 | 2 | 0.32 |
| 1 | 5 | 5 | 0.8 |

TABLE 1-continued

| $\mu$ (M.U.) | E (V/cm) | v ($\mu$m/sec) | $\Delta x$ ($\mu$m) |
|---|---|---|---|
| 1 | 10 | 10 | 1.6 |
| 2 | 1 | 2 | 0.32 |
| 2 | 2 | 4 | 0.64 |
| 2 | 5 | 10 | 1.6 |
| 2 | 10 | 20 | 3.2 |

TABLE 2

| d ($\mu$m) | D (cm$^2$/sec) | $\Delta x_D$ ($\mu$m) |
|---|---|---|
| 0.05 | 9.30 × 10$^{-8}$ | 1.73 |
| 0.1 | 4.65 × 10$^{-8}$ | 1.22 |
| 0.2 | 2.33 × 10$^{-8}$ | 0.86 |
| 0.5 | 9.30 × 10$^{-9}$ | 0.55 |
| 1 | 4.65 × 10$^{-9}$ | 0.39 |
| 2 | 2.33 × 10$^{-9}$ | 0.27 |
| 5 | 9.30 × 10$^{-10}$ | 0.17 |

Figure 6:
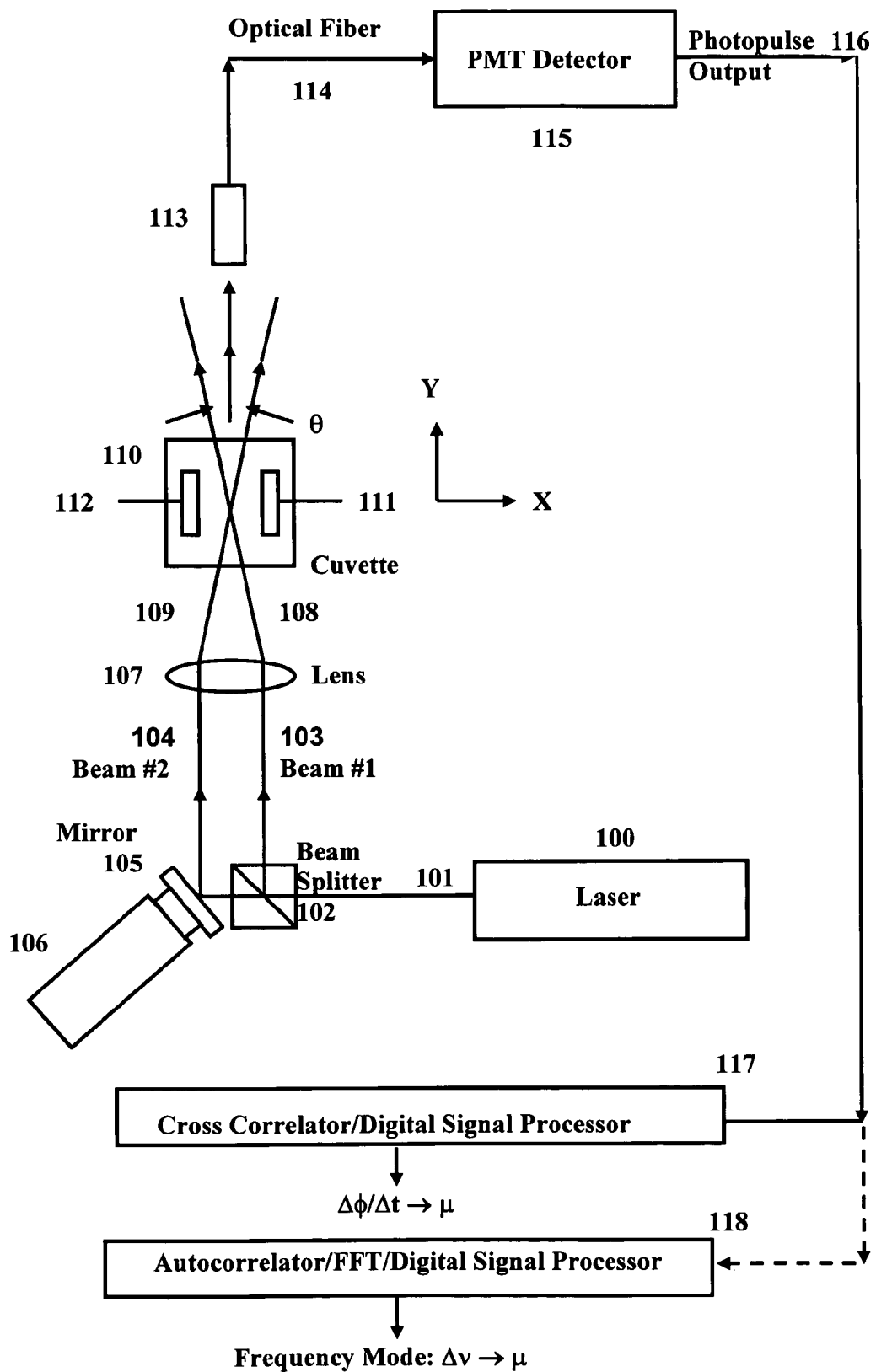
FIG. 6 shows a block diagram of yet another embodiment for light scattering analysis using cross-correlation for phase shift analysis of an optical detection signal.

FIG. 6 shows an exemplary schematic diagram of an apparatus to implement another exemplary embodiment as disclosed. The starting laser light beam 101 from a means, such as a laser source 100, is divided by a means, such as a beam splitter 102, into two light beams 103 and 104, labeled Beam #1 and Beam #2. The beam splitter can be configured optically to cause the two emerging light beams to have substantially equal intensities (i.e., approximately 50% of the intensity of the starting laser light beam). The direction of propagation of beam #2 can be rotated by 90-degrees with respect to beam #1 by a means, such as a deflecting mirror 105, attached to a modulator 106, which can be a piezo-electric transducer, causing the two beams 104 and 103 to be substantially parallel. The deflecting mirror 105 and modulator 106 are similar to, and perform a similar function as, the analogous components utilized in the first embodiment as disclosed above. A means, such as a focusing lens 107, can be used to redirect the two beams 108 and 109 to intersect in a region in the sample cuvette 110, said region located between the two electrodes 111 and 112. The two electrodes 111 and 112 are used to apply an electric field to the sample suspension, as previously described. This intersecting beam optical configuration can incorporate certain aspects of the related measurement technique of laser-Doppler velocimetry (LDV).

Figure 7:
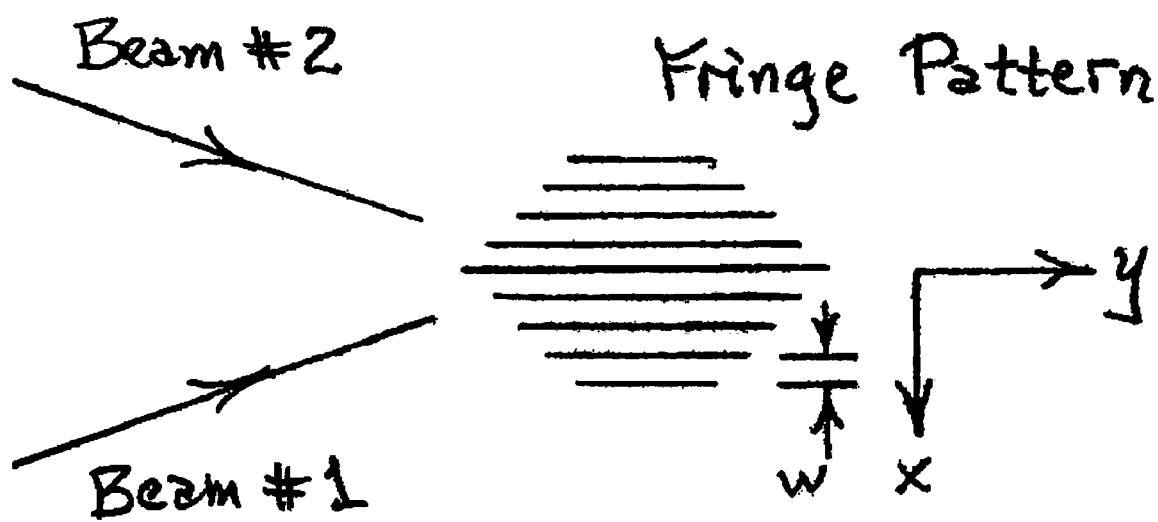
FIG. 7 shows a stylized view of an exemplary interference fringe pattern representing the alternating intensity maxima and minima in the x-y plane as may be produced by the second embodiment.

With this optical configuration, the phases of the oscillating electric fields associated with the two light waves 108 and 109, upon intersection, can have a fixed relative relationship to each other, for a given, fixed position of the deflecting mirror 105. That is, each of the two beams 108 and 109 maintains coherence with respect to the starting laser light wave 101. The difference in phase between the two intersecting waves at any point in the region of intersection is determined by the difference in the optical path lengths (OPLs) traversed to that point, i.e., $L_1+L_2+L_3$ (beam #2) versus $L_3+L_4$ (beam #1). Optical path lengths $L_1$, $L_2$ and $L_3$ correspond, respectively, to the light paths between beam splitter 102 and mirror 105; between mirror 105 and lens 107; and between lens 107 and the intersection point in cuvette 110. Similarly, optical path lengths $L_4$ and $L_5$ correspond, respectively, to the light paths between beam splitter 102 and lens 107; and between lens 107 and the intersection point in cuvette 110. Intersection of the two coherent light beams gives rise to an interference "fringe" pattern, including a number of small, parallel, equally-spaced disk-like regions of maximum illumination (intensity), alternating with regions of zero intensity. The spatial extent of the illumination profile defined by the fringe pattern and also the number of fringes contained therein depend on the cross-sectional widths of the intersecting light beams (each assumed to have a Gaussian intensity profile) and the angle of intersection (defined in the sample liquid), θ. FIG. 7 shows a stylized view of the fringe pattern, representing the intensity maxima in the x-y plane, where two adjacent fringes are separated by a distance w.

Charged particles in liquid suspension are caused to translate back and forth along the x-axis due to application of a periodic electric field along the same axis using a pair of parallel-plate electrodes 111 and 112 immersed in the sample liquid—the same as described for the first embodiment. Scattered light generated by the suspended particles located in the region illuminated by the intersecting light beams 108 and 109 is collected by a means, such as a light collection means 113, which can be similar to the means utilized in the first embodiment. The resulting collected scattered light is conveyed by suitable means, which can be an optical fiber 114, to a detection means, such as a light detector 115 or a PMT detector, as utilized in the first embodiment. The electronic output signal 116 produced by the light detector 115 is directed to a means, such as a signal processor 117, which can be a cross correlator and associated digital signal processor. Alternatively, the digital signal processor can be switchable between a cross-correlation analysis 117 of the photopulse signal with the drive signal and an autocorrelation analysis 118 of the photopulse signal, for measuring the electrophoretic mobility of the sample based on a phase shift analysis or a frequency shift analysis.

In the case in which the light collector 113 includes an optical collimator, having a narrow range of acceptance angles, with a collection axis coincident with the y-axis and intersecting the fringe pattern, the angle of scattering associated with the collected light rays is equal to θ/2. This scattering angle applies to both light beams, because the collection axis of the light collection means is assumed to bisect the angle defined (in the sample liquid) by the intersecting/diverging beams, θ.

The spacing of two adjacent fringes of intensity maxima, denoted by w, can be expressed as a simple function of angle θ, as reviewed by Miller et al, $$w = \lambda_o / [2n \sin(\theta/2)]. \tag{24}$$

Some numerical examples are useful, assuming $\lambda_o = 635$ nm (0.635 μm) and n=1.33 (water). In the case of θ=15°, w=1.83 μm, while for θ=20°, w=1.38 μm. For θ=25°, w=1.10 μm, while for θ=30°, w=0.92 μm. The use of a small intersection angle is required, given the fact that the corresponding scattering angle at which the scattered light is detected, θ/2, must be small in order to minimize the random fluctuations in the measured phase shift due to Brownian motion. This is the same consideration that was seen to apply in the first embodiment. Therefore, in practice the typical fringe spacing, w, lies in the approximate range of 1-2 μm.

As in the first embodiment, the apparatus employed in the second embodiment can use the technique of cross correlation to measure the phase shift of a detected scattered light wave associated with the translational motion of a particle induced by an applied electric field. In the second embodiment, it is useful to consider beam #2 as comprising, in effect, a kind of "reference" light wave, which "mixes" coherently with the light wave associated with beam #1. However, in this case, unlike the first embodiment, the mixing, or superposition, process occurs inside the sample cuvette, in the region from which the light scattering originates, rather than outside the cuvette, after the scattering process (inside) has already occurred. In this case, the purpose of the mixing, or superposition, process is to create a fringe pattern, as described above, in which the positions of the intensity maxima, to which the moving particles are exposed, are uniquely correlated to the phase of beam #2. However, notwithstanding this difference in optical design, the use of the cross correlation function to determine the phase shift associated with particle motion will be seen to strongly parallel its use for essentially the same purpose in the first embodiment.

A periodic translation of the light deflecting mirror can be performed in the manner of the first embodiment, by use of a suitable periodic drive voltage waveform applied to the modulator means, preferably a piezoelectric translator means, as utilized previously. The positions (i.e., along the x-axis in FIG. 6) of the intensity maxima that define the interference fringes described above depend on the phase of the light wave associated with beam #2 relative to the fixed phase of the wave associated with beam #1 when the two beams intersect. For example, an increase or decrease in the phase of beam #2 (at the point of intersection) equal to π radians causes the fringes to translate by a distance of w/2 along the x-axis, causing the regions that previously experienced maximum illumination to become completely dark, and vice-versa. An increase or decrease in the phase of beam #2 equal to 2π radians results in a fringe translation equal to w, which effectively results in no change whatsoever in the illuminated fringe pattern.

An exemplary periodic sawtooth drive voltage, $V_M(t)$, can be applied to the deflecting mirror modulator, just as was done in the first embodiment. As before, for purposes of discussion the drive signal can be considered in its ideal form, as a smooth, analog waveform. However, in actuality it more usefully takes the form of a uniform staircase of discrete digital steps, as shown in FIG. 4, appropriate for digital signal processing techniques. It is assumed that the periodic drive signal causes a linear extension, ΔS, in the piezoelectric transducer to which the light-deflecting mirror is attached. This process of translating the light deflecting mirror by distance ΔS results in an incremental decrease, ΔL, in the OPL of beam #2, defined by $L_1 + L_2 + L_3$ (discussed above).

The resulting decreases in $L_1$ and $L_2$, denoted by $\Delta L_1$ and $\Delta L_2$, respectively, are the same and therefore the total decrease in the OPL for these two legs of the light path is given by $$\Delta L_1 + \Delta L_2 = -\sqrt{2} \times \Delta S. \tag{25}$$

Calculation of the decrease in $L_3$, denoted by $\Delta L_3$, is more involved, given the fact that $L_3$ itself is a function of the distance, W, between the two parallel beams and the focal length, f, of the focusing lens. The resulting value for $\Delta L_3$ is given approximately (for small $\Delta L_1$) by, $$\Delta L_3 = (1/2) W \Delta L_1 / [(W/2)^2 + f^2]^{1/2}, \tag{26}$$

where the focal length is related to the beam spacing and the intersection angle by $$f = (W/2)/\tan(\theta/2). \tag{27}$$

As an example, in the case of θ=20°, the value for $\Delta L_3$ equals $-0.174 \Delta L_1$. From this value and use of Equation 25, one arrives at the decrease in the total OPL, equal to $-1.537 \Delta S$.

The corresponding change in phase, $\Delta \phi_2$, of beam #2 (to the point where it intersects beam #1) associated with the mirror extension, $\Delta S$, is given approximately (considering that most of the change in the OPL occurs in air, with n=1) in radians by, $$\Delta\phi_2 \approx 2\pi(\Delta L_1 + \Delta L_2 + \Delta L_3)/\lambda_o. \tag{28}$$

Assuming $\pi_o = 0.635$ μm and the value found above for the decrease in total OPL (for $\theta=20°$), the phase shift, $\Delta\phi_2$, equals $-15.2$ $\Delta S$ radians, where $\Delta S$ is expressed in microns (μm). Regardless of the angle of intersection, the phase shift in the light wave associated with beam #2 is proportional to $\Delta S$, just as was found for $\Delta\phi$ for the reference beam of the first embodiment, as described by Equation 12. A corresponding relation applies for $\Delta\phi_2$, where constant $Q_o$ (like $P_o$, previously) depends on the path geometry and resulting OPL of beam #2, as just discussed, $$\Delta\phi_2 = Q_o \times \Delta S. \tag{29}$$

Application of the periodic modulator drive voltage, $V_M(t)$, to the deflecting mirror modulator causes the fringes, representing maxima in illumination, to translate quasi-linearly with time along the x-axis during each sawtooth cycle (period). Of course, the fringe positions will move abruptly in steps of $\delta x$, corresponding to each discrete increase in applied driving voltage, $\delta_M$, equal to $V_{M,MAX}/N$, where N is the number of steps in the digital staircase waveform, as described for the first embodiment (FIG. 4). The fringes move in the same direction in discrete increments until an elapsed time equal to $T_M$, when they abruptly return to their original positions as the drive voltage returns to zero (or $\delta V_M$), at which time the process repeats. The maximum drive voltage, $V_{M,MAX}$, is adjusted so that the fringes translate by a total distance at least equal to the fringe spacing, w, during each cycle of the periodic drive voltage waveform. (In this way, each point along the x-axis between two adjacent fringes at the start of each cycle is exposed to the maximum illumination intensity during each modulation cycle.) The required voltage depends on the relationship between $\Delta\phi_2$ and $\Delta S$, and therefore on constant $Q_o$, as described by Equation 29. (This condition is analogous to the maximum extension, $\Delta S$, of the deflecting mirror, in order to ensure that the maximum phase shift, $\Delta\Phi$, of the reference beam is at least equal to $2\pi$ radians.)

As a result of the periodic, quasi-linear translation of the fringe pattern, the intensity maxima effectively "sweep" across the particles in the suspension. Again, it is conceptually simpler to confine the description to a single particle. As a maximum in illumination associated with a particular fringe sweeps across the particle, still assumed stationary, the intensity of the scattered light that it gives rise to increases and then decreases, in proportion to the intensity incident on the particle. The detected scattered light signal will therefore oscillate in magnitude at the same frequency, $\upsilon_M$, as the "sawtooth" waveform voltage, $V_M(t)$, used to drive the piezoelectric transducer means. Most importantly, there will be a fixed phase difference between the oscillating scattered light signal and the oscillating modulator drive voltage signal giving rise to the former. The particular value of the phase difference depends on the particular location of the particle along the x-axis—i.e., with respect to the positions of the fringes before they start to move (i.e., $V_M(t)=0$). Using the cross-correlation technique utilized in the first embodiment can be applied in this second embodiment, using the same CCF defined in Equation 10. As in the first embodiment, the CCF will exhibit a shape similar to that shown in stylized form in FIG. 3, with a peak value corresponding to a particular time-shift value, $\Delta t_1$. The latter value corresponds to a particular voltage drive value, $V_M(\Delta t_1)$, at which the phase shift, $\Delta\phi_2$, of beam #2 is such that the fringes have moved by such a distance as to cause one of them to be centered on the stationary particle, where the illumination is maximum, resulting in maximum scattered intensity.

Next, one considers motion of the single suspended particle along the x-axis, induced by an applied electric field, of magnitude E, along the same direction. The charged particle will therefore move either in the same direction as the moving fringes or in the opposite direction, depending on the sign of the charge on the particle and the direction of the applied electric field. The phase of the resulting detected scattered light signal will either increase or decrease with respect to the phase of the modulator drive voltage signal, depending on whether the particles move "with" the fringes or "against" them. Most of the description used in connection with the first embodiment can now be applied here, with minor modification. One assumes that the particle travels a distance $\Delta x$ during an elapsed time $\Delta t$. As before, the motion of the particle will cause the peak value of the CCF to shift in time, to either a larger or smaller time-shift value, depending on whether the field-induced particle motion is in the same direction as the fringe motion, or opposite. The additional amount of phase shift in the modulator drive voltage waveform, denoted now by $\Delta\phi$, needed to achieve a peak in the CCF due to particle translation $\Delta x$ during time $\Delta t$ is given (in radians) by $$\Delta\phi = 2\pi(\Delta x/w) \tag{30}$$

which, as before, can be rewritten in terms of μ, E and $\Delta t$, $$\Delta\phi = 2\pi(\mu E/w)\Delta t. \tag{31}$$

Therefore, the time rate of change in the phase shift for light beam #2 needed to continuously "track" the moving particle, thereby achieving a peak in the CCF, is given simply by, $$\Delta\phi/\Delta t = 2\pi(\mu E/w) \tag{32}$$

Substantially all of the description used in connection with the first embodiment can now be applied to the second embodiment, i.e., the same processing procedures apply here. The CCF, using N equally-spaced time-shift channels of width $\delta t$ (e.g., N=64, $\delta t$=20 μsec, as before) is constructed for a time $\Delta t_{CCF}$ corresponding to a multiple (e.g., 5, as before) of periodic drive voltage periods, $T_M$, in order to achieve improved statistical accuracy (i.e., signal/noise ratio) in the resulting CCF. The peak, or maximum, value of the CCF corresponds to a first computed value for the phase shift for light beam #2, denoted here as $\Delta\phi_1$, in parallel with the terminology used to describe the first embodiment. As in the first embodiment, an appropriate curve-fitting/averaging technique is optionally employed in order to improve the resolution in time-shift, and therefore in computed phase shift, $\Delta\phi_1$, beyond what would otherwise be obtained (i.e., simply $\Phi/N$), as discussed earlier. After an additional elapsed time equal to $\Delta t_{CCF}$, a second value of the phase shift for light beam #2, denoted by $\Delta\phi_2$, is obtained from the new (shifted) location of the peak in the CCF. The difference in these two phase-shift values, divided by $\Delta t_{CCF}$, thus yields the first computed value for the rate of change of the phase shift, $\Delta\phi/\Delta t|_1$, as described in detail for the first embodiment (Equation 21). As before, a running average of these time rate of change of phase shift values is computed for M measurement cycles, using the same direction of applied electric field. Then, the field direction is reversed, and the same procedure is repeated for another M measurement cycles (with a reversed sign to account for the reversal in the direction of the phase shift required to compensate for particle motion in the reverse direction). The resulting "grand" running average, $\Delta\phi/\Delta t$, of the successively determined rates of change in the phase shift, $\Delta\phi/\Delta t|_j$, results in a grand running average of corresponding values for the electrophoretic mobility, $\mu$, obtained by inverting equation 32. A grand running average of zeta potential values, $\zeta$, is then obtained from the running average values of $\mu$. This long-term, continuous averaging process greatly reduces the influence of spurious particle motion, unconnected with electric field-induced motion, due to Brownian motion and convective drift, as in the first embodiment.

The previous discussion has assumed the existence of a single particle moving under the applied electric field, giving rise to scattered light that depends on the position of the particle relative to the fringe pattern. However, it should be clear that the same description applies to the actual case, in which a large number of randomly located particles translate (and diffuse randomly) under the influence of the applied electric field and scatter light. At any given time some of the particles are located at fringe intensity maxima, scattering the most light, others lie in intensity minima, scattering no light, and still others lie at various points in between those extremes. As before, the purpose of the cross-correlation technique is to efficiently "extract" the useful information regarding the changing positions of all the particles over time. In this case the net scattered intensity detected from an ensemble of particles no longer resembles the simple, periodically varying waveform obtained from a single, uniformly translating particle. However, what is important is that there is a periodic component in the detected scattered intensity that is highly correlated with the location of the fringes (i.e., the intensity maxima) created by the intersection of the two coherent light waves. The location of these fringes, in turn, is well correlated with the phase of light beam #2 that, together with beam #1, gives rise to the fringe pattern, which can be varied periodically in quasi-linear fashion. Therefore, cross correlation of the net scattered intensity signal with the voltage drive signal used to modulate the phase of light beam #2 can be used efficiently and effectively to obtain stable, accurate and reproducible values for the electrophoretic mobility, as in the first embodiment. In particular, the cross correlation technique, together with the optional methods of curve-fitting/averaging of the CCF and subsequent grand averaging of intermediate values of $\Delta\phi$ and $\Delta\phi/\Delta t$ described earlier, can be used advantageously when the field-induced particle velocity is very small. Therefore, electrophoretic mobilities can be determined relatively accurately in cases where the applied field is very small or when the mobility is inherently very small.

Figure 2B:
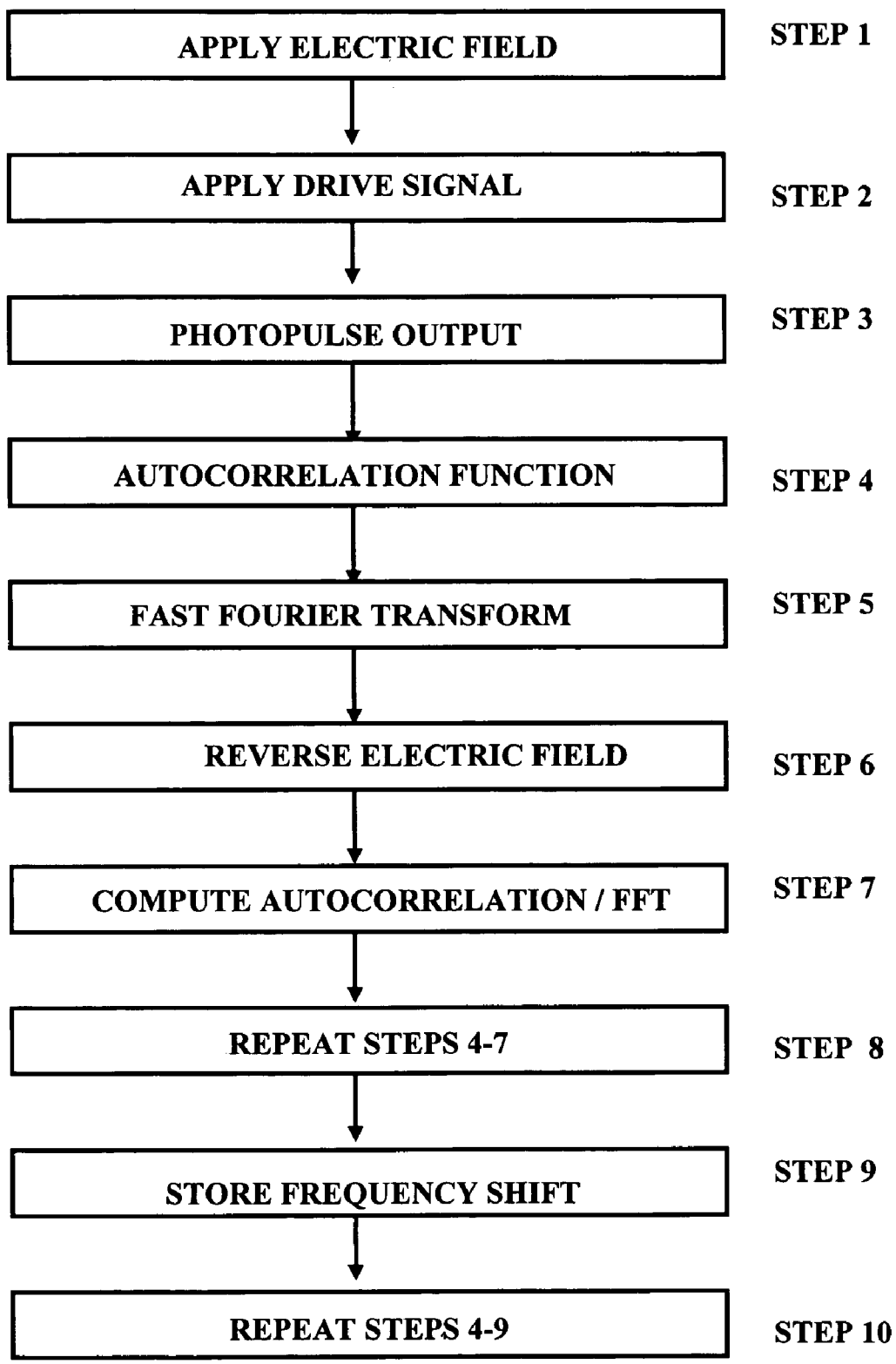
FIG. 2b shows an exemplary flowchart diagram for light scattering analysis using autocorrelation for frequency shift analysis of an optical detection signal.

Executable instructions of a computer program, for example, the steps shown in FIGS. 2a and 2b, can be embodied in any computer readable medium for use by or in connection with an instruction execution system, apparatus, or device, such as a computer based system, processor containing system, or other system that can fetch the instructions from the instruction execution system, apparatus, or device and execute the instructions.

As used here, a "computer readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non exhaustive list) of the computer readable medium can include the following: an electrical connection having one or more wires, a portable computer diskette, a random access memory (RAM), a read only memory (ROM), an erasable programmable read only memory (EPROM or Flash memory), an optical fiber, and a portable compact disc read only memory (CDROM).

It will be appreciated by those of ordinary skill in the art that the concepts and techniques described here can be embodied in various specific forms without departing from the essential characteristics thereof. The presently disclosed embodiments are considered in all respects to be illustrative and not restrictive. The scope of the invention is indicated by the appended claims, rather than the foregoing description, and all changes that come within the meaning and range of equivalence thereof are intended to be embraced.

What is claimed is:

1. A device for electrophoretic mobility determination using light scattering phase analysis comprising:
   a laser emitting laser light along a path;
   a beam splitter positioned along the path to transmit a first portion of the laser light and to reflect a second portion of the laser light;
   an oscillating mirror positioned to deflect one of the first and second portions of the laser light in response to a drive signal;
   a cuvette holding a sample disposed to output a composite light wave based on input of at least one of the first and second portions of the laser light, the cuvette having at least two electrodes disposed along sides of the cuvette to create an electric field;
   a scattered light detector disposed to output a photopulse signal based on input of the composite light wave; and
   a processor for measuring the electrophoretic mobility of the sample based on a phase shift analysis using cross-correlation of the photopulse signal with the drive signal, and outputting values capable of being stored in a computer memory for display of results based on the electrophoretic mobility measurements.

2. The device according to claim 1, comprising a switched electric source connected to the at least two electrodes to produce a switched electric field between the at least two electrodes.

3. The device according to claim 1, comprising a neutral density filter which attenuates the laser light to output a filtered laser light.

4. The device according to claim 3, comprising a lens for focusing the filtered laser light.

5. The device according to claim 4, comprising a mirror for deflecting the focused laser light.

6. The device according to claim 1, wherein the first portion of the laser light is passed through the sample to output a light scattering component with a scattering angle.

7. The device according to claim 6, comprising a diffuser for producing a diffused component of the second portion of the laser light by diffusing the second portion of the laser light.

8. The device according to claim 7, comprising a coherent mixer for combining the diffused component of the second portion of the laser light with the light scattering component scattered by the sample to produce the composite light wave.

9. The device according to claim 8, comprising an optical collector disposed at a scattering angle for collecting the composite light wave.

10. The device according to claim 1, wherein the processor is a digital signal processor which is switchable between the cross-correlation analysis of the photopulse signal with the drive signal and an autocorrelation analysis of the photopulse signal, for measuring the electrophoretic mobility of the sample based on a phase shift analysis or a frequency shift analysis, respectively.

11. The device according to claim 1, comprising a lens for redirecting the first and the second portions of the laser light to intersect.

12. The device according to claim 11, wherein the cuvette passes the first and second portions of the laser light through the sample to output a light scattering component with a scattering angle.

13. The device according to claim 12, wherein the first portion and the second portion of the laser light intersect in the cuvette.

14. The device according to claim 13, comprising an optical collector disposed for collecting the light scattering component.

15. The device according to claim 14, wherein the processor is a digital signal processor which is switchable between a cross-correlation analysis of the photopulse signal with the drive signal and an autocorrelation analysis of the photopulse signal, for measuring the electrophoretic mobility of the sample based on a phase shift analysis or a frequency shift analysis, respectively.

16. An apparatus for determining electrophoretic mobility using light scattering phase analysis comprising:
means for emitting a laser light along a path;
means for transmitting a first portion of the laser light and reflecting a second portion of the laser light;
means for deflecting one of the first and second portions of the laser light in response to a drive signal;
means for holding a sample, to receive at least one of the first and second portions of the laser light under an electric field, and to output a composite light wave;
means for outputting a photopulse signal based on the composite light wave; and
means for measuring the electrophoretic mobility of the sample based on a phase shift analysis using cross-correlation of the photopulse signal with the drive signal, and outputting values capable of being stored in a computer memory for display of results based on the electrophoretic mobility measurements.

17. The apparatus according to claim 16, comprising means for producing the electric field.

18. The apparatus according to claim 16, comprising means for attenuating the laser light to output a filtered laser light.

19. The apparatus according to claim 18, comprising means for focusing the filtered laser light.

20. The apparatus according to claim 19, comprising means for deflecting the focused laser light.

21. The apparatus according to claim 16, wherein the first portion of the laser light is passed through the sample to output a light scattering component with a scattering angle.

22. The apparatus according to claim 21, comprising means for receiving the second portion of the laser light and producing a diffused component of the second portion of the laser light.

23. The apparatus according to claim 22, comprising means for combining the diffused component of the second portion of the laser light with the light scattering component scattered by the sample to produce the composite light wave.

24. The apparatus according to claim 23, comprising means for collecting the composite light wave at a scattering angle.

25. The apparatus according to claim 16, wherein the means for measuring electrophoretic mobility is switchable between the cross-correlation analysis of the photopulse signal with the drive signal and an autocorrelation analysis of the photopulse signal, for measuring the electrophoretic mobility of the sample based on a phase shift analysis or a frequency shift analysis, respectively.

26. The apparatus according to claim 16, comprising means for redirecting the first and the second portions of the laser light to intersect.

27. The apparatus according to claim 26, wherein the first and second portions of the laser light are passed through the sample to output a light scattering component with a scattering angle.

28. The apparatus according to claim 27, wherein the sample is disposed at a location where the first portion and the second portion of the laser light intersect.

29. The apparatus according to claim 28, comprising means for collecting the light scattering component.

30. The apparatus according to claim 29, wherein the means for measuring electrophoretic mobility is switchable between a cross-correlation analysis of the photopulse signal with the drive signal and an autocorrelation analysis of the photopulse signal, for measuring the electrophoretic mobility of the sample based on a phase shift analysis or a frequency shift analysis, respectively.

31. A method for determining electrophoretic mobility using scattering light phase analysis comprising:
emitting a laser light along a path;
transmitting a first portion of the laser light and reflecting a second portion of the laser light;
deflecting one of the first and second portions of the laser light in response to a drive signal;
holding a sample to receive at least one of the first and second portions of the laser light under an electric field and output a composite light wave;
outputting a photopulse signal based on the composite light wave; and
measuring the electrophoretic mobility of the sample based on a phase shift analysis using cross-correlation of the photopulse signal with the drive signal, and outputting values capable of being stored in a computer memory for display of results based on the electrophoretic mobility measurements.

32. The method according to claim 31, comprising producing the electric field.

33. The method according to claim 31, comprising attenuating the laser light to output a filtered laser light.

34. The method according to claim 33, comprising focusing the filtered laser light.

35. The method according to claim 34, comprising deflecting the focused laser light.

36. The method according to claim 31, wherein the first portion of the laser light is passed through the sample to output a light scattering component with a scattering angle.

37. The method according to claim 36, comprising producing a diffused component of the second portion of the laser light.

38. The method according to claim 37, comprising combining the diffused component of the second portion of the laser light with the light scattering component scattered by the sample to produce the composite light wave.

39. The method according to claim 38, comprising collecting the composite light wave.

40. The method according to claim 31, wherein the measuring the electrophoretic mobility of the sample is switchable between the cross-correlation analysis of the photopulse signal with the drive signal and an autocorrelation analysis of the photopulse signal, for measuring the electrophoretic mobility of the sample based on a phase shift analysis or a frequency shift analysis, respectively.

41. The method according to claim 31, comprising redirecting the first and the second portions of the laser light to intersect.

42. The method according to claim 41, wherein the first and second portions of the laser light are passed through the sample to output a light scattering component with a scattering angle.

43. The method according to claim 42, wherein the sample is disposed at a location where the first portion and the second portion of the laser light intersect.

44. The method according to claim 43, comprising collecting the light scattering component.

45. The method according to claim 44, wherein the measuring the electrophoretic mobility of the sample is switchable between the cross-correlation analysis of the photopulse signal with the drive signal and an autocorrelation analysis of the photopulse signal, for measuring the electrophoretic mobility of the sample based on a phase shift analysis or a frequency shift analysis, respectively.

46. The device according to claim 1, wherein at least one of fitting and averaging is applied based on the cross-correlation of the photopulse signal with the drive signal for improved peak time resolution.

47. The device according to claim 46, wherein a phase shift is measured and a running average of a rate of change of the phase shift is calculated based on the cross-correlation of the photopulse signal with the drive signal.

48. The apparatus according to claim 16, wherein at least one of fitting and averaging is applied based on the cross-correlation of the photopulse signal with the drive signal for improved peak time resolution.

49. The apparatus according to claim 48, wherein a phase shift is measured and a running average of a rate of change of the phase shift is calculated based on the cross-correlation of the photopulse signal with the drive signal.

50. The method according to claim 31, wherein at least one of fitting and averaging is applied based on the cross-correlation of the photopulse signal with the drive signal for improved peak time resolution.

51. The method according to claim 50, wherein a phase shift is measured and a running average of a rate of change of the phase shift is calculated based on the cross correlation of the photopulse signal with the drive signal.

* * * * *